US007902223B2

(12) United States Patent
Dorsch et al.

(10) Patent No.: US 7,902,223 B2
(45) Date of Patent: Mar. 8, 2011

(54) PHENYL DERIVATIVES AS FACTOR XA INHIBITORS

(75) Inventors: Dieter Dorsch, Ober-Ramstadt (DE); Bertram Cezanne, Mörfelden-Walldorf (DE); Christos Tsaklakidis, Weinheim (DE); Werner Mederski, Zwingenberg (DE); Johannes Gleitz, Darmstadt (DE); Christopher Barnes, Bad Soden (DE)

(73) Assignee: Merck Patent GmbH, Darmstadt (DE)

( * ) Notice: Subject to any disclaimer, the term of this patent is extended or adjusted under 35 U.S.C. 154(b) by 1931 days.

(21) Appl. No.: 10/486,238

(22) PCT Filed: Jul. 12, 2002

(86) PCT No.: PCT/EP02/07798
§ 371 (c)(1), (2), (4) Date: Feb. 9, 2004

(87) PCT Pub. No.: WO03/013531
PCT Pub. Date: Feb. 20, 2003

(65) Prior Publication Data
US 2004/0235828 A1    Nov. 25, 2004

(30) Foreign Application Priority Data
Aug. 8, 2001 (DE) ................... 101 39 060

(51) Int. Cl.
C07D 215/38 (2006.01)
A61K 31/04 (2006.01)

(52) U.S. Cl. .......... 514/309; 514/310; 514/312; 514/313; 346/153; 346/157; 346/159; 346/148; 346/149; 346/162

(58) Field of Classification Search .......... 546/153, 546/157, 159, 148, 149, 162; 514/312, 313, 514/309, 310
See application file for complete search history.

(56) References Cited

U.S. PATENT DOCUMENTS
3,279,880 A    10/1966    Straley et al.

FOREIGN PATENT DOCUMENTS
| DE | 28 15 820 | 10/1978 |
| WO | 00 71508 | 11/2000 |
| WO | 00 71510 | 11/2000 |
| WO | 00 71511 | 11/2000 |
| WO | 02 057236 | 7/2002 |

OTHER PUBLICATIONS

Freshney, R. Ian, Culture of Animal Cells: A manuel of Basis Technique, New York, pp. 4-6, 2000.*
Dermer, Gerald B., "Another Anniversary for the War on Cancer", Bio/technology, vol. 12, p. 320, Mar. 1994.*
L. Desaubry et al., "Synthesis of a Conformationally . . . Adenine Derivative", *Tetrahedron Letters*, 36(24), pp. 4249-4252 (1995).

* cited by examiner

*Primary Examiner* — D. Margaret Seaman
(74) *Attorney, Agent, or Firm* — Millen, White, Zelano, Branigan, P.C.

(57) ABSTRACT

Novel compounds of the formula (I), in which D, W, X, Y, T and $R^1$ are as defined in Patent Claim 1, are inhibitors of coagulation factor Xa and can be employed for the prophylaxis and/or therapy of thromboembolic diseases and for the treatment of tumors.

26 Claims, No Drawings

PHENYL DERIVATIVES AS FACTOR XA INHIBITORS

The invention relates to compounds of the formula I

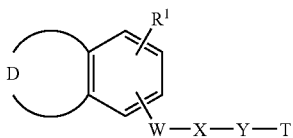

in which

D is a saturated, fully or partially unsaturated 3- to 4-membered alkylene chain, in which from 1 to 3 carbon atoms may be replaced by N and/or 1 or 2 carbon atoms may be replaced by 1 or 2 O and/or 1 or 2 S atoms, but where at most up to 3 carbon atoms have been replaced, and where, in addition, a mono-, di- or trisubstitution of the alkylene chain and/or of a nitrogen located therein by Hal, A, —[C($R^3$)$_2$]$_n$—Ar, —[C($R^3$)$_2$]$_n$-Het, —[C($R^3$)$_2$]$_n$-cycloalkyl, $OR^2$, N($R^2$)$_2$, $NO_2$, CN, $COOR^2$, CON($R^2$)$_2$, $NR^2COA$, $NR^2SO_2A$, $COR^2$, $SO_2NR^2$ and/or S(O)$_m$A may occur, and where, furthermore, a $CH_2$ group in the alkylene chain may also be replaced by a C=O group, $R^1$ is H, Hal, A, $OR^2$, N($R^2$)$_2$, $NO_2$, CN, $COOR^2$, CON($R^2$)$_2$, —[C($R^3$)$_2$]$_n$—Ar, —[C($R^3$)$_2$]$_n$-Het or —[C($R^3$)$_2$]$_n$-cycloalkyl $R^2$ is H, A, —[C($R^3$)$_2$]$_n$—Ar, —[C($R^3$)$_2$]$_n$-Het or —[C($R^3$)$_2$]$_n$- cycloalkyl, $R^3$ is H or A, W is —C($R^2$)$_2$—, —[C($R^2$)$_2$]$_2$—, —OC($R^2$)$_2$— or —$NR^2$C($R^2$)$_2$—, X is $CONR^2$, $CONR^2C(R^3)_2$, —C($R^3$)$_2NR^2$ or —C($R^3$)$_2NR^2C(R^3)_2$, Y is alkylene, cycloalkylene, Het-diyl or Ar-diyl, T is a monocyclic or bicyclic, saturated or unsaturated heterocyclic ring having from 1 to 4 N, O and/or S atoms which is monosubstituted, disubstituted or trisubstituted by carbonyl oxygen and may furthermore be monosubstituted, disubstituted or trisubstituted by Hal, A, [C($R^3$)$_2$]$_n$—Ar, —[C($R^3$)$_2$]$_n$-Het, —[C($R^3$)$_2$]$_n$-cycloalkyl, $OR^2$, N($R^2$)$_2$, $NO_2$, CN, $COOR^2$, CON($R^2$)$_2$, $NR^2COA$, $NR^2CON(R^2)_2$, $NR^2SO_2A$, $COR^2$, $SO_2NR^2$ and/or S(O)$_m$A, A is unbranched or branched alkyl having 1-6 carbon atoms, in which one or two $CH_2$ groups may be replaced by O or S atoms and/or by —CH=CH— groups and/or in addition 1-7 H atoms may be replaced by F, Ar is phenyl, naphthyl or biphenyl, each of which is unsubstituted or monosubstituted, disubstituted or trisubstituted by Hal, A, $OR^3$, N($R^3$)$_2$, $NO_2$, CN, $COOR^3$, CON($R^3$)$_2$, $NR^3COA$, $NR^3CON(R^3)_2$, $NR^3SO_2A$, $COR^3$, $SO_2N(R^3)_2$ or S(O)$_m$A, Het is a monocyclic or bicyclic, saturated, unsaturated or aromatic heterocyclic ring having from 1 to 4 N, O and/or S atoms, which may be unsubstituted or monosubstituted, disubstituted or trisubstituted by carbonyl oxygen, Hal, A, —[C($R^3$)$_2$]$_n$—Ar, —[C($R^3$)$_2$]$_n$-$Het^1$, —[C($R^3$)$_2$]$_n$-cycloalkyl, $OR^2$, N($R^2$)$_2$, $NO_2$, CN, $COOR^2$, CON($R^2$)$_2$, $NR^2COA$, $NR^2CON(R^2)_2$, $NR^2SO_2A$, $COR^2$, $SO_2NR^2$ and/or S(O)$_m$A, $Het^1$ is a monocyclic or bicyclic, saturated, unsaturated or aromatic heterocyclic ring having 1 or 2 N, O and/or S atoms, which may be unsubstituted or monosubstituted or disubstituted by carbonyl oxygen, Hal, A, $OR^2$, N($R^2$)$_2$, $NO_2$, CN, $COOR^2$, CON($R^2$)$_2$, $NR^2COA$, $NR^2CON(R^2)_2$, $NR^2SO_2A$, $COR^2$, $SO_2NR^2$ and/or S(O)$_m$A, Hal is F, Cl, Br or I, n is 0, 1 or 2, m is 0, 1 or 2, and pharmaceutically usable derivatives, solvates and stereoisomers thereof, including mixtures thereof in all ratios.

The invention had the object of finding novel compounds having valuable properties, in particular those which can be used for the preparation of medicaments.

It has been found that the compounds of the formula I and salts thereof have very valuable pharmacological properties and are well tolerated. In particular, they exhibit factor Xa-inhibiting properties and can therefore be employed for combating and preventing thromboembolic diseases, such as thrombosis, myocardial infarction, arteriosclerosis, inflammation, apoplexia, angina pectoris, restenosis after angioplasty and claudicatio intermittens.

The compounds of the formula I according to the invention may furthermore be inhibitors of the coagulation factors factor VIIa, factor IXa and thrombin in the blood coagulation cascade.

Aromatic amidine derivatives having an antithrombotic action are disclosed, for example, in EP 0 540 051 B1, WO 98/28269, WO 00/71508, WO 00/71511, WO 00/71493, WO 00/71507, WO 00/71509, WO 00/71512, WO 00/71515 or WO 00/71516. Cyclic guanidines for the treatment of thromboembolic diseases are described, for example, in WO 97/08165. Aromatic heterocyclic compounds having factor Xa-inhibitory activity are disclosed, for example, in WO 96/10022. Substituted N-[(aminoiminomethyl)phenylalkyl]azaheterocyclylamides as factor Xa inhibitors are described in WO 96/40679.

The antithrombotic and anticoagulant effect of the compounds according to the invention is attributed to the inhibitory action against activated coagulation protease, known by the name factor Xa, or to the inhibition of other activated serine proteases, such as factor VIIa, factor IXa or thrombin.

Factor Xa is one of the proteases involved in the complex process of blood coagulation. Factor Xa catalyses the conversion of prothrombin into thrombin. Thrombin cleaves fibrinogen into fibrin monomers, which, after crosslinking, make an elementary contribution to thrombus formation. Activation of thrombin may result in the occurrence of thromboembolic diseases. However, inhibition of thrombin may inhibit the fibrin formation involved in thrombus formation.

The inhibition of thrombin can be measured, for example, by the method of G. F. Cousins et al. in *Circulation* 1996, 94, 1705-1712.

Inhibition of factor Xa can thus prevent the formation of thrombin. The compounds of the formula I according to the invention and salts thereof engage in the blood coagulation process by inhibiting factor Xa and thus inhibit the formation of thrombi.

The inhibition of factor Xa by the compounds according to the invention and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220-223.

The inhibition of factor Xa can be measured, for example, by the method of T. Hara et al. in *Thromb. Haemostas.* 1994, 71, 314-319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation.

The inhibition of factor VIIa by the compounds according to the invention and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73-81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa by the compounds according to the invention and the measurement of the anticoagulant and antithrombotic activity can be determined by conventional in-vitro or in-vivo methods. A suitable method is described, for example, by J. Chang et al. in *Journal of Biological Chemistry* 1998, 273, 12089-12094.

The compounds according to the invention may furthermore be used for the treatment of tumours, tumour diseases and/or tumour metastases. A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57-59.

The publications listed below describe an antitumoral action of TF-VII and factor Xa inhibitors in various types of tumour:

K. M. Donnelly et al. in Thromb. Haemost. 1998; 79: 1041-1047;
E. G. Fischer et al. in J. Clin. Invest. 104: 1213-1221 (1999);
B. M. Mueller et al. in J. Clin. Invest. 101: 1372-1378 (1998);
M. E. Bromberg et al. in Thromb. Haemost. 1999; 82: 88-92

The compounds of the formula I can be employed as medicament active ingredients in human and veterinary medicine, in particular for the treatment and prevention of thromboembolic diseases, such as thrombosis, myocardial infarction, arteriosclerosis, inflammation, apoplexia, angina pectoris, restenosis after angioplasty, claudicatio intermittens, venous thrombosis, pulmonary embolism, arterial thrombosis, myocardial ischaemia, unstable angina and strokes based on thrombosis.

The compounds according to the invention are also employed for the treatment or prophylaxis of atherosclerotic diseases, such as coronary arterial disease, cerebral arterial disease or peripheral arterial disease. The compounds are also employed in combination with other thrombolytic agents in the case of myocardial infarction, furthermore for prophylaxis for reocclusion after thrombolysis, percutaneous transluminal angioplasty (PTCA) and coronary bypass operations.

The compounds according to the invention are furthermore used for the prevention of rethrombosis in microsurgery, furthermore as anticoagulants in connection with artificial organs or in haemodialysis.

The compounds are furthermore used in the cleaning of catheters and medical aids in vivo in patients, or as anticoagulants for the preservation of blood, plasma and other blood products in vitro. The compounds according to the invention are furthermore used in diseases in which blood coagulation makes a crucial contribution to the course of the disease or represents a source of secondary pathology, such as, for example, in cancer, including metastasis, inflammatory diseases, including arthritis, and diabetes.

The compounds according to the invention are furthermore used for the treatment of migraine (F. Morales-Asin et al., Headache, 40, 2000, 45-47).

In the treatment of the diseases described, the compounds according to the invention are also employed in combination with other thrombolytically active compounds, such as, for example, with "tissue plasminogen activator" t-PA, modified t-PA, streptokinase or urokinase. The compounds according to the invention are administered either at the same time as or before or after the other substances mentioned.

Particular preference is given to simultaneous administration with aspirin in order to prevent recurrence of the thrombus formation. The compounds according to the invention are also used in combination with blood platelet glycoprotein receptor (IIb/IIIa) antagonists, which inhibit blood platelet aggregation.

The invention relates to the compounds of the formula I and salts thereof and to a process for the preparation of compounds of the formula I according to Claims 1-13 and pharmaceutically usable derivatives, solvates and stereoisomers thereof, characterised in that a) for the preparation of a compound of the formula I in which W is —OC($R^2$)$_2$— or —N$R^2$C($R^2$)$_2$—,
a compound of the formula II

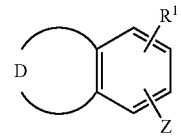

in which
Z is OH or NH$R^2$,
and $R^1$, $R^2$ and D are as defined above, with the proviso that any further OH and/or amino group present is protected, is reacted with a compound of the formula III $$L-C(R^2)_2—X—Y-T \qquad III$$

in which
L is Cl, Br or I, and $R^2$, X, Y and T are as defined in above, and any protecting group is subsequently cleaved off, b) for the preparation of a compound of the formula I in which X is CON$R^2$ or CON$R^2$C($R^3$)$_2$,
a compound of the formula IV

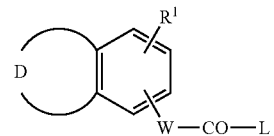

in which
L is Cl, Br, I or a free or reactively functionally modified OH group, and $R^1$, W and D are as defined above, with the proviso that any further OH and/or amino group present is protected,
is reacted with a compound of the formula V $$Z'-Y-T \qquad V$$

in which
Z' is NH$R^2$ or NH$R^2$C($R^3$)$_2$,
and $R^2$, Y and T are as defined above, and any protecting group is subsequently cleaved off,
and/or a base or acid of the formula I is converted into one of its salts.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, monohydrates or dihydrates or alcoholates.

The term pharmaceutically usable derivatives is taken to mean, for example, the salts of the compounds according to the invention and also so-called prodrug compounds.

The term prodrug derivatives is taken to mean compounds of the formula I which have been modified with, for example, alkyl or acyl groups, sugars or oligopeptides and which are rapidly cleaved in the organism to give the effective compounds according to the invention. These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

For all radicals which occur more than once, such as, for example, A, their meanings are independent of one another. Above and below, the radicals or parameters Y, T, W, $R^1$ and $R^2$ are as defined under the formula I, unless expressly stated otherwise.

D is preferably —CO—NH—CO, —CO—NH—CH$_2$—, —NH—CH=CH—, —O—CH=CH—, —N=CH—O—, —N=CH—NH—, —NH—NH—CO—, —NH—N=N—, —NH—CO—CH$_2$—, —NH—CO—O—, —N=CH—S—, —NH—CO—S—, —NH—CO—NH—, —O—NH—CO—, —NH—O—CO—, —N=CH—CH=CH—, —CH=N—CH=CH—, —N=N—CH=CH—, —N=CH—N=CH—, —N=CH—CH=N—, —N=N—N=CH—, —NH—CO—CH=CH—, —NH—CH=CH—CO—, —NH—CO—CH$_2$—CH$_2$—, —NH—CH$_2$—CH$_2$—CO—, —NH—CO—N=CH—, —N=CH—NH—CO—, —NH—CO—NH—CO—, —NH—CO—NH—CH$_2$—, —CH=N—N=CH—, —N$^-$—S$^+$=N—, —O—CH$_2$—O—, furthermore —CH=N—NH—CO—, —CH=N—NH—, —NH—N=CH—, —O—CH$_2$CH$_2$—O—, —CO—NH—NH—CO—, —N=N—NH—CO—, —O—CO—NH—CH$_2$— or —O—CO—NH—CO—, furthermore —(CH$_2$)$_3$— or —(CH$_2$)$_4$—.

D is particularly preferably —CH=N—CH=CH—, —O—CH$_2$—O—, —CH=CH—NH—, —S—CH=N—, —NH—N=CH—, —O—CH$_2$CH$_2$—O—, —N=CH—CH=N— or —N$^-$—S$^+$=N—.

D may be monosubstituted disubstituted or trisubstituted, preferably by Hal, A, OR$^2$ or N(R$^2$)$_2$, and/or a CH$_2$ group in the alkylene chain may also be replaced by a C=O group. Very particular preference is given to monosubstitution by A or NH$_2$.

A is alkyl, is unbranched (linear) or branched, and has 1, 2, 3, 4, 5, 6, 7, 8, 9 or 10 carbon atoms. A is preferably methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3- , 2,2-, 2,3- or 3,3-dimethylbutyl, 1- or 2-ethylbutyl, 1-ethyl-1-methylpropyl, 1-ethyl-2methylpropyl, 1,1,2- or 1,2,2-trimethylpropyl, furthermore preferably, for example, trifluoromethyl. A is very particularly preferably alkyl having 1-6 carbon atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cycloalkyl is preferably cyclopropyl, cyclobutyl, cyclopentyl, cyclohexyl or cycloheptyl.

Alkylene is preferably methylene, ethylene, propylene, butylene, pentylene or hexylene, furthermore branched alkylene.

—COA (acyl) is preferably acetyl, propionyl, furthermore also butyryl, pentanoyl, hexanoyl or, for example, benzoyl.

Hal is preferably F, Cl or Br, but also I.

$R^1$ is preferably H.

W is preferably —C(R$^{2'}$)$_2$—, —[C(R$^{2'}$)$_2$]$_2$—, —OC(R$^{2'}$)$_2$— or —NR$^{2'}$C(R$^{2'}$)$_2$—,
in which R$^{2'}$ is H, A' or phenyl,
and A' is alkyl having 1, 2, 3, 4, 5 or 6 carbon atoms.

X is preferably CONH, CONHCH$_2$, CH$_2$NH or CH$_2$NHCH$_2$, very particularly preferably CONH.

Y is preferably alkylene or Ar-diyl, particularly preferably methylene, ethylene, propylene, or 1,4-phenylene which is unsubstituted or monosubstituted by A or F, furthermore also pyridinediyl, preferably pyridine-2,5-diyl. Y is, in particular, 1,3- or 1,4-phenylene which is unsubstituted or monosubstituted by methyl, ethyl or propyl.

Ar is, for example, unsubstituted phenyl, naphthyl or biphenyl, furthermore preferably phenyl, naphthyl or biphenyl, each of which is, for example, monosubstituted, disubstituted or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl or aminocarbonyl.

Het is, for example, 2- or 3-furyl, 2- or 3-thienyl,1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazoi-2- or -5-yl, 1,2,4-thiadiazol-3- or -5-yl, 1,2,3-thiadiazol4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Het can thus, for example, also be 2,3-dihydro-2-, -3-, 4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, 4-, -5-, -6-, -7- or -8-quinolyl, 1,2,3,4-tetrahydro-1-,-2-,-3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)-phenyl or alternatively 3,4-dihydro-2H-1,5-benzodioxepin-6- or -7-yl, furthermore preferably 2,3-dihydrobenzofuranyl or 2,3-dihydro-2-oxo-furanyl.

T is preferably a monocyclic saturated or unsaturated heterocyclic ring having 1 or 2 N and/or O atoms, which may be monosubstituted or disubstituted by carbonyl oxygen, OH or OA.

T is particularly preferably, for example, 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2,6-dioxopiperidin 1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-methoxy-6-oxopiperazin-1-yl, 2-azabicyclo[2.2.2]octan-3-on-2-yl, very particularly preferably 2-oxopiperidin-1-yl.

The compounds of the formula I may have one or more chiral centres and therefore occur in various stereoisomeric forms. The formula I covers all these forms.

Accordingly, the invention relates in particular to the compounds of the formula I in which at least one of the said radicals has one of the preferred meanings indicated above. Some preferred groups of compounds may be expressed by the following sub-formulae Ia to Il, which conform to the formula I and in which the radicals not designated in greater detail are as defined under the formula I, but in which in Ia D is a saturated, fully or partially unsaturated 3- to 4-membered alkylene chain, in which from 1 to 3 carbon atoms may be replaced by N and/or 1 or 2 carbon atoms may be replaced by 1 or 2 O and/or 1 or 2 S atoms, but where at most up to 3 carbon atoms are replaced, and where, in addition, a mono-, di- or trisubstitution of the alkylene chain and/or of a nitrogen located therein by Hal, A, $OR^2$ or $N(R^2)_2$ may occur, and where, furthermore, a $CH_2$ group in the alkylene chain may also be replaced by a C=O group;

in Ib D is a saturated, fully or partially unsaturated 3- to 4-membered alkylene chain, in which from 1 to 3 carbon atoms may be replaced by N and/or 1 or 2 carbon atoms may be replaced by 1 or 2 O and/or 1 or 2 S atoms, but where at most up to 3 carbon atoms are replaced, and where, in addition, a mono-, di- or trisubstitution of the alkylene chain and/or of a nitrogen located therein by A or $NH_2$ may occur, and where, furthermore, a $CH_2$ group in the alkylene chain may also be replaced by a C=O group;

in Ic D is —CO—NH—CO, —CO—NH—$CH_2$—, —NH—CH=CH—, —O—CH=CH—, —N=CH—O—, —N=CH—NH—, —NH—NH—CO—, —NH—N=N—, —NH—CO—$CH_2$—, —NH—CO—O—, —N=CH—S—, —NH—CO—S—, —NH—CO—NH—, —O—NH—CO—, —NH—O—CO—, —N=CH—CH=CH—, —CH=N—CH=CH—, —N=N—CH=CH—, —N=CH—N=CH—, —N=CH—CH=N—, —N=N—N=CH—, —NH—CO—CH=CH—, —NH—CH=CH—CO—, —NH—CO—$CH_2$—$CH_2$—, —NH—$CH_2$—$CH_2$—CO—, —NH—CO—N=CH—, —N=CH—NH—CO—, —NH—CO—NH—CO—, —NH—CO—NH—$CH_2$—, —CH=N—N=CH—, —$N^-$—$S^+$=N—, —O—$CH_2$—O—, —CH=N—NH—CO—, —CH=CH—NH—, —NH—N=CH—, —O—$CH_2CH_2$—O—, —CO—NH—NH—CO—, —N=N—NH—CO—, —O—CO—NH—$CH_2$—, —O—CO—NH—CO—, —$(CH_2)_3$—, —CO—$(CH_2)_2$—, —$(CH_2)_4$— or —CO—$(CH_2)_3$—;

in Id $R^1$ is H;

in Ie W is —$C(R^{2'})_2$—, —$[C(R^{2'})_2]_2$—, —$OC(R^{2'})_2$— or —$NR^{2'}C(R^{2'})_2$—, $R^{2'}$ is H, A' or phenyl, A' is alkyl having 1, 2, 3, 4, 5 or 6 carbon atoms;

in If X is CONH;

in Ig Y is alkylene, Ar-diyl or Het-diyl;

in Ih Y is methylene, ethylene, propylene, or 1,4-phenylene or pyridinediyl, each of which is unsubstituted or monosubstituted by A, Cl or F;

in Ii Y is 1,3- or 1,4-phenylene which is unsubstituted or monosubstituted by methyl, ethyl, propyl, Cl, F or trifluoromethyl;

in Ij T is a monocyclic or bicyclic, saturated or unsaturated heterocyclic ring having 1 or 2 N and/or O atoms, which may be monosubstituted or disubstituted by carbonyl oxygen, OH or OA;

in Ik T is 2-oxopiperidin-1-yl, 2-oxopyrrolidin-1-yl, 2-oxo-1H-pyridin-1-yl, 3-oxomorpholin4-yl, 4-oxo-1H-pyridin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-azabicyclo[2.2.2]octan-3-on-2-yl or 2-methoxy-6-oxopiperazin-1-yl;

in Il D is —CO—NH—CO, —CO—NH—$CH_2$—, —NH—CH=CH—, —O—CH=CH—, —N=CH—O—, —N=CH—NH—, —NH—NH—CO—, —NH—N=N—, —NH—CO—$CH_2$—, —NH—CO—O—, —N=CH—S—, —NH—CO—S—, —NH—CO—NH—, —O—NH—CO—, —NH—O—CO—, —N=CH—CH=CH—, —CH=N—CH=CH—, —N=N—CH=CH—, —N=CH—N=CH—, —N=CH—CH=N—, —N=N—N=CH—, —NH—CO—CH=CH—, —NH—CH=CH—CO—, —NH—CO—$CH_2$—$CH_2$—, —NH—$CH_2$—$CH_2$—CO—, —NH—CO—N=CH—, —N=CH—NH—CO—, —NH—CO—NH—CO—, —NH—CO—NH—$CH_2$—, —CH=N—N=CH—, —$N^-$—$S^+$=N—, —O—$CH_2$—O—, —CH=N—NH—CO—, —CH=CH—NH—, —NH—N=CH—, —O—$CH_2CH_2$—O—, —CO—NH—NH—CO—, —N=N—NH—CO—, —O—CO—NH—$CH_2$—, —O—CO—NH—CO—, —$(CH_2)_3$—, —CO—$(CH_2)_2$—, —$(CH_2)_4$—, —CO—$(CH_2)_3$—, —$(CH_2)_2$—CO— or —$(CH_2)_3$—CO—, and where, in addition, a mono- or disubstitution of the alkylene chain and/or of a nitrogen located therein by A or $NH_2$ may occur, $R^1$ is H, W is —$C(R^{2'})_2$—, —$[C(R^{2'})_2]_2$—, —$OC(R^{2'})_2$— or —$NR^{2'}C(R^{2'})_2$—, $R^{2'}$ is H, A' or phenyl, A' is alkyl having 1, 2, 3, 4, 5 or 6 carbon atoms, X is CONH, Y is 1,3- or 1,4-phenylene which is unsubstituted or monosubstituted by methyl, ethyl, propyl, Cl, F or trifluoromethyl, T is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1, 3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-azabicyclo[2.2.2]octan-3-on-2-yl or 2-methoxy-6-oxopiperazin-1-yl;

and pharmaceutically usable derivatives, solvates and stereoisomers thereof, including mixtures thereof in all ratios.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds of the formula I.

The starting compounds of the formulae II, III, IV and V are generally known. If they are novel, however, they can be prepared by methods known per se.

All compounds of the following formula VI (where R=H or methyl; n=3, 4 or 5) can be synthesised in accordance with the following scheme.

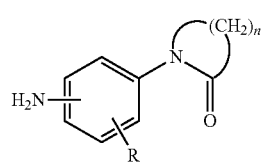

VI

For example, synthesis of 1-(4-amino-2-methylphenyl)piperidin-2-one:

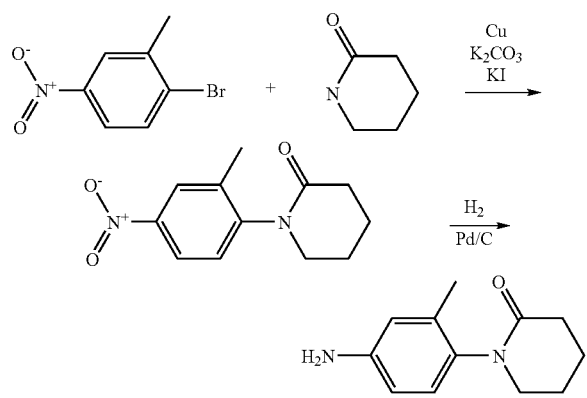

Alternative synthesis:

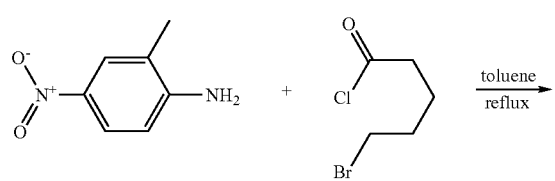

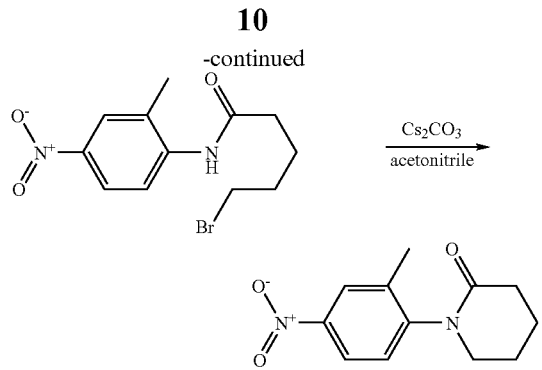

Synthesis of the phenylpiperidone unit without a methyl group:

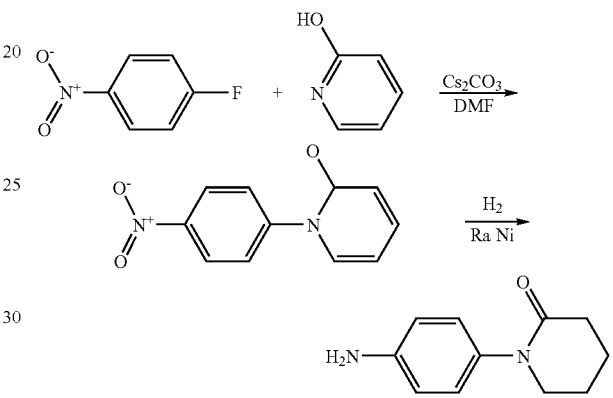

The invention therefore also relates to compounds of the formula VI and salts thereof.

A base of the formula VI can be converted into the associated acid-addition salt using an acid, for example by reaction of equivalent amounts of the base and the acid in an inert solvent, such as ethanol, followed by evaporation. Thus, it is possible to use inorganic acids, for example sulfuric acid, nitric acid, hydrohalic acids, such as hydrochloric acid or, hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, or laurylsulfuric acid.

Compounds of the formula I can preferably be obtained by reacting compounds of the formula II with compounds of the formula III.

The reaction is generally carried out in an inert solvent, in the presence of an acid-binding agent, preferably an alkali or alkaline-earth metal hydroxide, carbonate or bicarbonate or another salt of a weak acid of the alkali or alkaline-earth metals, preferably of potassium, sodium, calcium or caesium. The addition of an organic base, such as triethylamine, dimethylaniline, pyridine or quinoline, or of an excess of the phenol component of the formula II or the alkylation derivative of the formula III may also be favourable. The reaction time is between a few minutes and 14 days, depending on the conditions used, and the reaction temperature is between about 0° and 150°, normally between 20° and 130°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Compounds of the formula I can furthermore preferably be obtained by reacting compounds of the formula IV with compounds of the formula V. The reaction is generally carried out in an inert solvent and under conditions as indicated above. In the compounds of the formula IV, L is preferably Cl, Br, I or a free or reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy). Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart;). Activated esters are advantageously formed in situ, for example through addition of HOBt or N-hydroxysuccinimide.

The reaction is generally carried out in an inert solvent, in the presence of an acid-binding agent, preferably an organic base, such as DIPEA, triethylamine, dimethylaniline, pyridine or quinoline, or an excess of the carboxyl component of the formula IV. The addition of an alkali or alkaline-earth metal hydroxide, carbonate or bicarbonate or another salt of a weak acid of the alkali or alkaline-earth metals, preferably of potassium, sodium, calcium or caesium, may also be favourable. The reaction time is between a few minutes and 14 days, depending on the conditions used, and the reaction temperature is between about −30° and 140°, normally between −10° and 90°, in particular between about 0° and about 70°. Suitable inert solvents are those mentioned above.

Compounds of the formula I can furthermore be obtained by liberating compounds of the formula I from one of their functional derivatives by treatment with a solvolysing or hydrogenolysing agent.

Preferred starting materials for the solvolysis or hydrogenolysis are those which conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' is an amino-protecting group, instead of an HN group, and/or those which carry a hydroxyl-protecting group instead of the H atom of a hydroxyl group, for example those which conform to the formula I, but carry a —COOR" group, in which R" is a hydroxyl-protecting group, instead of a —COOH group. Preferred starting materials are also the oxadiazole derivatives, which can be converted into the corresponding amidino compounds.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but which are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut and Mtr groups can, for example, preferably be cleaved off using TFA in dichloromethane or using approximately 3 to 5N HCl in dioxane at 15-30°, the FMOC group using an approximately 5 to 50% solution of dimethylamine, diethylamine or piperidine in DMF at 15-30°.

Protecting groups which can be removed hydrogenolytically (for example CBZ, benzyl or the liberation of the amidino group from its oxadiazole derivative)) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using NaOH or KOH in water, water/THF or water/dioxane, at temperatures between 0 and 100°.

Free amino groups can furthermore be acylated in a conventional manner using an acid chloride or anhydride or alkylated using an unsubstituted or substituted alkyl halide, or reacted with $CH_3-C(=NH)-OEt$, advantageously in an inert solvent, such as dichloromethane or THF and/or in the presence of a base, such as triethylamine or pyridine, at temperatures between −60 and +30°.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, or laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline-earth metal salts, or into the corresponding ammonium salts using bases (for example sodium hydroxide, potassium hydroxide, sodium carbonate or potassium carbonate). It is also possible to use physiologically acceptable organic bases, such as, for example, ethanolamine.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to, the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or physiologically acceptable salts thereof for the preparation of a medicament (pharmaceutical preparation), in particular by non-chemical methods. They can be converted here into a suitable dosage form together with at least one solid, liquid and/or semi-liquid excipient or assistant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and, if desired, excipients and/or assistants.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders or also as nasal sprays. The novel compounds may also be lyophilised and the resultant lyophilisates used, for example, to prepare injection preparations. The preparations indicated may be sterilised and/or comprise assistants, such as lubricants, preservatives, stabilisers and/or wetting agents, emulsifying agents, salts for modifying the osmotic pressure, buffer substances, colorants and flavours and/or a plurality of further active ingredients, for example one or more vitamins.

The compounds of the formula I and physiologically acceptable salts thereof can be used for combating and preventing thromboembolic diseases, such as thromboses, myocardial infarction, arteriosclerosis, inflammation, apoplexia, angina pectoris, restenosis after angioplasty, claudicatio intermittens, tumours, tumour diseases and/or tumour metastases.

In general, the substances according to the invention are preferably administered in doses between about 1 and 500 mg, in particular between 5 and 100 mg, per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

The invention furthermore relates to the use of compounds of the formula I and/or pharmaceutically usable derivatives, solvates and stereoisomers thereof, including mixtures thereof in all ratios, for the preparation of a medicament for the treatment of thromboses, myocardial infarction, arteriosclerosis, inflammation, apoplexia, angina pectoris, restenosis after angioplasty, claudicatio intermittens, migraine, tumours, tumour diseases and/or tumour metastases, in combination with at least one further medicament active ingredient.

Above and below, all temperatures are given in ° C. In the following examples, "conventional work-up" means that water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) $M^+$

FAB (fast atom bombardment) $(M+H)^+$

ESI (electrospray ionisation) $(M+H)^+$ (unless specified otherwise)

EXAMPLE 1

N-[4-(2-Oxopiperidin-1-yl)phenyl]-2-(1-aminoisoquinolin-7-yloxy)-pentanamide ("AA")

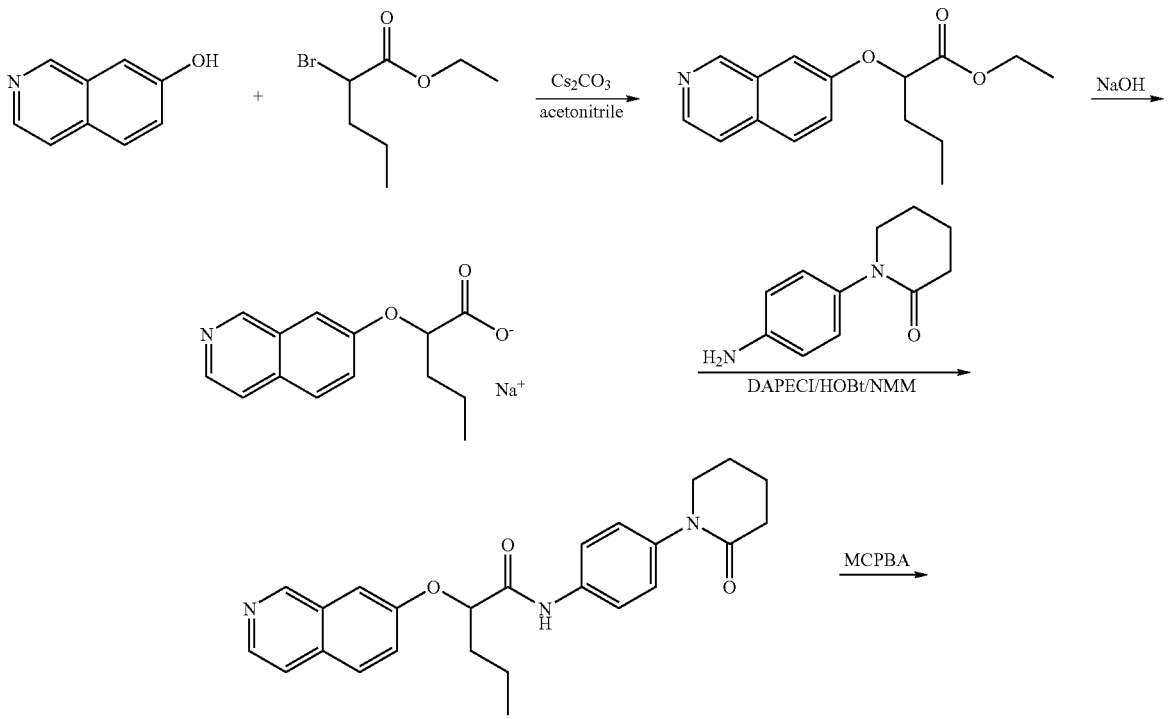

-continued

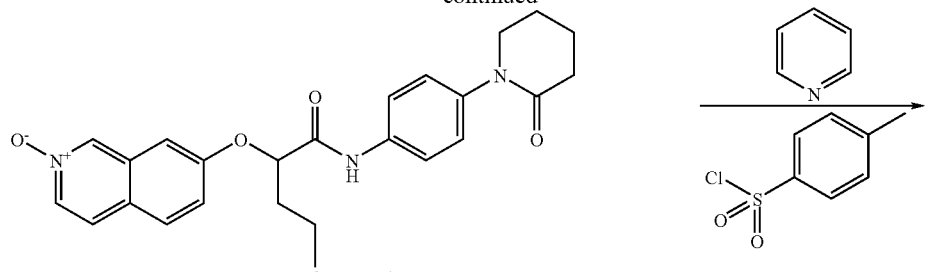

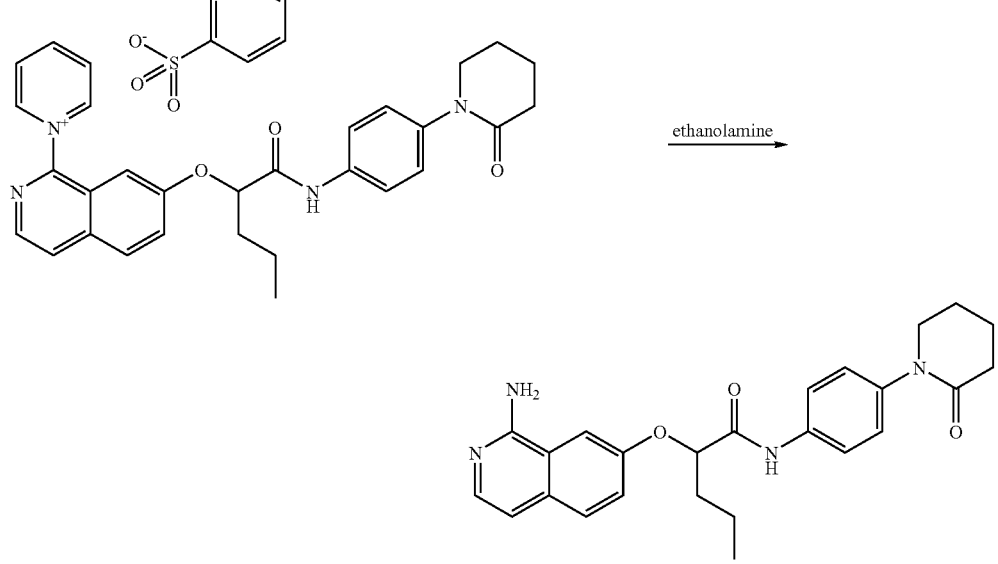

6.70 g (20.6 mmol) of caesium carbonate are added to a solution of 3.00 g (20.7 mmol) of 7-hydroxyisoquinoline and 4.33 g (20.7 mmol) of ethyl 2-bromopentanoate in 30 ml of acetonitrile, and the mixture is stirred at room temperature for 18 hours. The reaction mixture is filtered, and the filtrate is evaporated, giving ethyl 2-(isoquinolin-7-yloxy)-pentanoate as a colourless solid; ESI 274.

10 ml of water and 840 mg (21.0 mmol) of sodium hydroxide are added to a solution of 5.20 g (19.0 mmol) of ethyl 2-(isoquinolin-7-yloxy)-pentanoate in 50 ml of methanol, and the mixture is stirred at room temperature for 42 hours. The solvent is removed by distillation, giving 2-(isoquinolin-7-yloxy)pentanoic acid sodium salt as a colourless solid; ESI 246.

390 ml (3.55 mmol) of 4-methylmorpholine are added to a solution of 940 mg (3.52 mmol) of 2-(isoquinolin-7-yloxy) pentanoic acid sodium salt, 670 mg (3.52 mmol) of 1-(4-aminophenyl)piperidin-2-one, 670 mg (3.52 mmol) of N-(3-dimethylaminopropyl)-N'-ethylcarbodiimide hydrochloride (DAPECI) and 480 mg (3.56 mmol) of 1-hydroxybenzotriazole (HOBt) in 2 ml of DMF, and the mixture is stirred at room temperature for 18 hours. The reaction mixture is introduced into water, and the precipitate is filtered off, giving N-[4-(2-oxopiperidin-1-yl)phenyl]-2-(isoquinolin-7-yloxy)pentanamide as a colourless solid; ESI 418.

464 mg (2.69 mmol) of 3-chloroperbenzoic acid are added to a solution of 600 mg (1.44 mmol) of N-[4-(2-oxopiperidin-1-yl)phenyl]-2-(isoquinolin-7-yloxy)pentanamide in 5 ml of acetone, and the mixture is stirred at room temperature for 18 hours. The reaction mixture is evaporated, and the residue is partitioned between ethyl acetate and saturated sodium hydrogencarbonate solution. The organic phase is evaporated, giving N-[4-(2-oxopiperidin-1-yl)phenyl]-2-(2-oxyisoquinolin-7-yloxy)pentanamide as a colourless solid; ESI 434.

137 mg (0.40 mmol) of 4-toluenesulfonyl chloride are added to a solution of 270 mg (0.435 mmol) of N-[4-(2-oxopiperidin-1-yl)phenyl]-2-(2-oxyisoquinolin-7-yloxy) pentanamide in 2 ml of pyridine, and the mixture is stirred at room temperature for 18 hours. The solvent is removed by distillation, giving 1-(7-{1-[4-(2-oxopiperidin-1-yl)phenylcarbamoyl]-butoxy}isoquinolin-1-yl)pyridinium toluene-4-sulfonate as a reddish solid.

The crude 1-(7-{1-[4-(2-oxopiperidin-1-yl)phenylcarbamoyl]butoxy}-isoquinolin-1-yl)pyridinium toluene4-sulfonate obtained in this way is dissolved in 4 ml of ethanolamine, and the mixture is stirred at room temperature for 42 hours. The reaction mixture is introduced into water and extracted with ethyl acetate. The organic phase is evaporated, and the residue is chromatographed on a silica-gel column, giving N-[4-(2-oxopiperidin-1-yl)phenyl]-2-(1-aminoisoquinolin-7-yloxy)pentanamide ("AA") as a colourless solid; ESI 433.

The following are obtained analogously:
N-[4-(2-oxopiperidin-1-yl)phenyl]-2-(1-aminoisoquinolin-7-yloxy)-2-phenylacetamide ("AB"), ESI 467;
N-[4-(2-oxopiperidin-1-yl)phenyl]-2-(isoquinolin-7-yloxy)-2-phenylacetamide, ESI 452;
N-[4-(2-oxopiperidin-1-yl)phenyl]-2-(isoquinolin-7-yloxy) pentanamide, ESI 418;

N-[4-(2-oxopiperidin-1-yl)phenyl]-2-(1-aminoisoquinolin-7-yloxy)acetamide, ESI 391;
N-[4-(2-oxopiperidin-1-yl)phenyl]-2-(isoquinolin-7-yloxy)acetamide, ESI 376;
N-[4-(2-oxopyrrolidin-1-yl)-3-methylphenyl]-2-(isoquinolin-7-yloxy)-pentanamide, ESI 418;
N-[4-(2-oxopiperidin-1-yl)-3-methylphenyl]-2-(isoquinolin-7-yloxy)-pentanamide, ESI 432;
N-[4-(2-oxoazepan-1-yl)-3-methylphenyl]-2-(isoquinolin-7-yloxy)-pentanamide, ESI 446;
N-[4-(2-oxopiperidin-1-yl)-3-methylphenyl]-2-(isoquinolin-7-yloxy)acetamide, ESI 390;
N-[3-methyl-4-(2-oxopiperidin-1-yl)phenyl]-2-(isoquinolin-7-yloxy)-2-(2-fluorophenyl)acetamide, ESI 484;
N-[4-(2-oxo-1H-pyrazin-1-yl)phenyl]-2-(isoquinolin-7-yloxy)pentanamide, ESI 415.

EXAMPLE 2

N-[4-(2-Oxopiperidin-1-yl)-3-methylphenyl]-2-(2,1,3-benzothiadiazol-5-ylamino)-2-phenylacetamide The preparation is carried out analogously to the following reaction scheme:

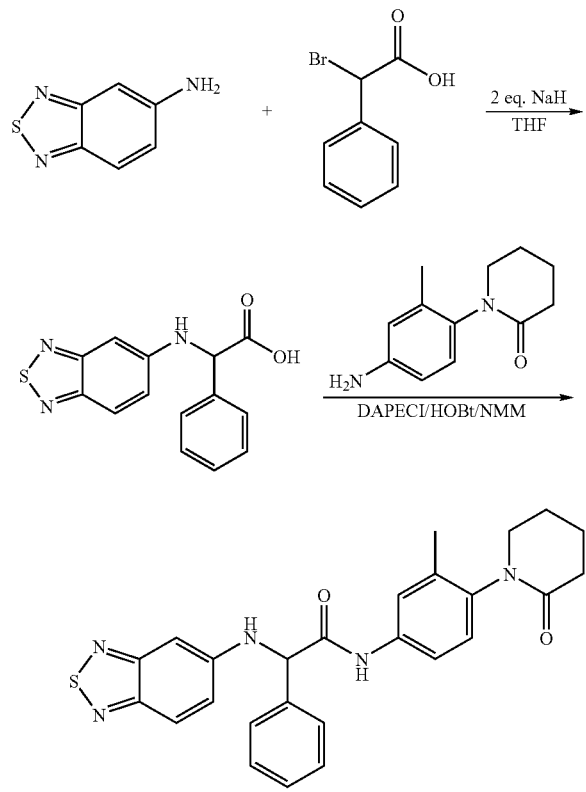

The following compounds are obtained analogously:
N-[4-(2-oxopiperidin-1-yl)-3-methylphenyl]-2-(1,3-benzodioxol-5-yl-amino)-2-phenylacetamide,
N-[4-(2-oxopiperidin-1-yl)-3-methylphenyl]-2-(indol-5-ylamino)-2-phenylacetamide,
N-[4-(2-oxopiperidin-1-yl)-3-methylphenyl]-2-(2-methylbenzimidazol-5-ylamino)-2-phenylacetamide,
N-[4-(2-oxopiperidin-1-yl)-3-methylphenyl]-2-(benzothiazol-6-ylamino)-2-phenylacetamide,
N-[4-(2-oxopiperidin-1-yl)-3-methylphenyl]-2-(isoquinolin-7-ylamino)-2-phenylacetamide,
N-[4-(2-oxopiperidin-1-yl)-3-methylphenyl]-2-(isoquinolin-6-ylamino)-2-phenylacetamide,
N-[4-(2-oxopiperidin-1-yl)-3-methylphenyl]-2-(1H-indazol-6-ylamino)-2-phenylacetamide,
N-[4-(2-oxopiperidin-1-yl)-3-methylphenyl]-2-(1H-indazol-5-ylamino)-2-phenylacetamide,
N-[4-(2-oxopiperidin-1-yl)-3-methylphenyl]-2-(2,3-dihydrobenzo-1,4-dioxin-6-ylamino)-2-phenylacetamide,
N-[4-(2-oxopiperidin-1-yl)-3-methylphenyl]-2-(quinoxalin-6-ylamino)-2-phenylacetamide.

Pharmacological Data

Affinity to Receptors

TABLE 1

| Compound No. | FXa-IC$_{50}$ [M] | TF/FVIIa-IC$_{50}$ [M] |
|---|---|---|
| "AA" | $3.5 \times 10^{-7}$ | $2.2 \times 10^{-7}$ |
| "AB" | $3.5 \times 10^{-7}$ | $2.0 \times 10^{-7}$ |

EXAMPLE 3

Synthesis of 1-(4-amino-2-methylphenyl)piperidin-2-one

A mixture of 5.00 g (23.1 mmol) of 2-bromo-5-nitrotoluene, 2.28 g (23.0 mmol) of 2-piperidone, 2.56 g (40 mmol) of finely powdered copper, 4.98 g (36.0 mmol) of potassium carbonate and 5.98 g (36 mmol) of potassium iodide is heated at 140° C. for 48 hours. The reaction mixture is introduced into water, the mixture is filtered, and the residue is washed with water. The residue is taken up in ethyl acetate and re-filtered. The filtrate is dried and evaporated, giving 1-(4-nitro-2-methylphenyl)piperidin-2-one as a yellowish solid; ESI 235.

800 mg of water-moist palladium on activated carbon are added to a solution of 4.00 g (17.1 mmol) of 1-(4-nitro-2-methylphenyl)piperidin-2-one in 150 ml of methanol, and the mixture is hydrogenated at room temperature and atmospheric pressure for 22 hours. The reaction mixture is filtered, and the filtrate is evaporated, giving 1-(4-amino-2-methylphenyl)piperidin-2-one as a colourless solid; ESI 205.

EXAMPLE 4

The following compounds are obtained analogously to Example 1:
N-[4-(3-oxomorpholin-4-yl)phenyl]-(S)-2-(1-aminoisoquinolin-7-yl-oxy)-4-methylpentanamide, hydrochloride, ESI 449;

N-[3-methyl-4-(3-oxomorpholin4-yl)phenyl]-(S)-2-(1-aminoisoquinolin-7-yl-oxy)-4-methylpentanamide, hydrochloride, ESI 463;
N-[4-(2-oxo-2H-pyridin-1-yl)phenyl]-(S)-2-(1-aminoisoquinolin-7-yl-oxy)-4-methylpentanamide, hydrochloride, ESI 449;
N-[4-(3-oxomorpholin-4-yl)phenyl]-2-(1-aminoisoquinolin-7-yloxy)-pentanamide, hydrochloride, ESI 435;
N-[4-(3-oxomorpholin4-yl)phenyl]-2-(1-aminoisoquinolin-7-yloxy)-2-(2-chlorophenyl)acetamide,
N-[4-(3-oxo-2H-pyridazin-2-yl)phenyl]-2-(1-aminoisoquinolin-7-yl-oxy)-4-methylpentanamide,
N-[4-(2-oxo-1H-pyrazin-1-yl)phenyl]-2-(1-aminoisoquinolin-7-yloxy)-4-methylpentanamide,
N-[4-(2-oxopiperazin-1-yl)phenyl]-2-(1-aminoisoquinolin-7-yloxy)-4-methylpentanamide,
N-[4-(2-oxo-1,3-oxazinan-3-yl)phenyl]-2-(1-aminoisoquinolin-7-yl-oxy)-4-methylpentanamide,
N-[4-(2-oxo-3H-thiazol-3-yl)phenyl]-2-(1-aminoisoquinolin-7-yloxy)-4-methylpentanamide,
N-[4-(2-oxooxazolidin-3-yl)phenyl]-2-(1-aminoisoquinolin-7-yloxy)-4-methylpentanamide,
N-[3-methyl-4-(2-oxooxazolidin-3-yl)phenyl]-2-(1-aminoisoquinolin-7-yloxy)-4-methylpentanamide,
N-[4-(2-oxotetrahydropyrimidin-1-yl)phenyl]-2-(1-aminoisoquinolin-7-yloxy)-4-methylpentanamide,
N-[4-(2-oxoimidazolidin-1-yl)phenyl]-2-(1-aminoisoquinolin-7-yl-oxy)-4-methylpentanamide,
N-[3-methyl-4-(2-oxoazepan-1-yl)phenyl]-2-(1-aminoisoquinolin-7-yloxy)pentanamide, hydrochloride, ESI 461;
N-[3-methyl-4-(2-oxopiperidin-1-yl)phenyl]-2-(1-aminoisoquinolin-7-yloxy)pentanamide, hydrochloride, ESI 447;
N-[3-methyl4-(2-oxopiperidin-1-yl)phenyl]-2-(1-aminoisoquinolin-7-yloxy)acetamide, hydrochloride, ESI 405;
N-[3-trifluoromethyl4-(2-azabicyclo[2.2.2]octan-3-on-2-yl)phenyl]-2-(1-aminoisoquinolin-7-yloxy)pentanamide, ESI 527;
N-[4-(2-oxopiperidin-1-yl)phenyl]-2-(1-aminoisoquinolin-7-yloxy)-propionamide, hydrochloride, ESI 405;
N-[4-(2-oxopiperidin-1-yl)phenyl]-2-(1-aminoisoquinolin-7-yloxy)-butyramide, hydrochloride, ESI 419;
N-[3-methyl-4-(2-oxopyrrolidin-1-yl)phenyl]-2-(1-aminoisoquinolin-7-yloxy)butyramide, hydrochloride, ESI 419;
N-[4-(2-oxopiperidin-1-yl)phenyl]-2-(1-aminoisoquinolin-7-yloxy)-pentanamide, hydrochloride, ESI 433;
N-[4-(2-oxopyrrolidin-1-yl)phenyl]-2-(1-aminoisoquinolin-7-yloxy)-hexanamide, hydrochloride, ESI 433;
N-[3-methyl-4-(2-oxopiperidin-1-yl)phenyl]-2-(1-aminoisoquinolin-7-yloxy)hexanamide, hydrochloride, ESI 461;
N-[4-(2-oxo-2H-pyridin-1-yl)phenyl]-2-(1-aminoisoquinolin-7-yloxy)-butyramide, hydrochloride, ESI 415;
N-[4-(2-oxo-2H-pyridin-1-yl)phenyl]-2-(1-aminoisoquinolin-7-yl-oxy)pentanamide, hydrochloride, ESI 429;
N-[3-chloro-4-(2-oxopyrrolidin-1-yl)phenyl]-2-(1-aminoisoquinolin-7-yloxy)pentanamide, hydrochloride, ESI 453;
N-[3-methyl-4-(2-oxopiperidin-1-yl)phenyl]-2-(1-aminoisoquinolin-7-yloxy)butyramide, hydrochloride, ESI 433;
N-[4-(2-oxopiperidin-1-yl)phenyl]-2-(1-aminoisoquinolin-7-yl-oxy)hexanamide, hydrochloride, ESI 447;
N-[4-(2-oxopiperidin-1-yl)phenyl]-2-(1-aminoisoquinolin-7-yloxy)-4-methylpentanamide, hydrochloride, ESI 447;
N-[3-methyl-4-(2-oxopiperidin-1-yl)phenyl]-2-(1-aminoisoquinolin-7-yloxy)-4-methylpentanamide, hydrochloride, ESI 461;
N-[4-(2-oxo-2H-pyridin-1-yl)phenyl]-2-(1-aminoisoquinolin-7-yloxy)-4-methylpentanamide, hydrochloride, ESI 443;
N-[4-(2-oxopiperidin-1-yl)phenyl]-2-(1-aminoisoquinolin-7-yloxy)-2-(2-fluorophenyl)acetamide, hydrochloride, ESI 485;
N-[3-methyl-4-(2-oxopiperidin-1-yl)phenyl]-2-(1-aminoisoquinolin-7-yloxy)-2-(2-fluorophenyl)acetamide, hydrochloride, ESI 499;
N-[4-(2-oxo-2H-pyridin-1-yl)phenyl]-(R)-2-(1-aminoisoquinolin-7-yl-oxy)-4-methylpentanamide, hydrochloride, ESI 443;
N-[4-(2-oxo-2H-pyridin-1-yl)phenyl]-2-(1-aminoisoquinolin-7-yloxy)-4,4-dimethylpentanamide, hydrochloride, ESI 457;
N-[4-(2-oxo-2H-pyridin-1-yl)phenyl]-2-(1-aminoisoquinolin-7-yloxy)-2-(2-fluorophenyl)acetamide, hydrochloride, ESI 481;
N-[4-(3-oxomorpholin-4-yl)phenyl]-2-(1-aminoisoquinolin-7-yl-oxy)butyramide, hydrochloride, ESI 421;
N-[3-methyl-4-(3-oxomorpholin-4-yl)phenyl]-2-(1-aminoisoquinolin-7-yloxy)butyramide, hydrochloride, ESI 435;
N-[3-methyl-4-(3-oxomorpholin-4-yl)phenyl]-2-(1-aminoisoquinolin-7-yloxy)pentanamide, hydrochloride, ESI 449;
N-[3-chloro-4-(2-oxo-2H-pyridin-1-yl)phenyl]-2-(1-aminoisoquinolin-7-yloxy)-4-methylpentanamide, hydrochloride, ESI 477;
N-[4-(3-oxomorpholin4-yl)phenyl]-2-(1-aminoisoquinolin-7-yloxy)-2-(2-fluorophenyl)acetamide, hydrochloride, ESI 487;
N-[3-methyl-4-(3-oxomorpholin4-yl)phenyl]-2-(1-aminoisoquinolin-7-yloxy)4-methylpentanamide, hydrochloride, ESI 463;
N-[3-chloro-4-(2-oxopyrrolidin-1-yl)phenyl]-2-(1-aminoisoquinolin-7-yloxy)-2-(2-fluorophenyl)acetamide, hydrochloride, ESI 505;
N-[3-chloro-4-(2-oxo-2H-pyridin-1-yl)phenyl]-2-(1-aminoisoquinolin-7-yloxy)butyramide, ESI 449;
N-[2-fluoro-4-(2-oxo-2H-pyridin-1-yl)phenyl]-2-(1-aminoisoquinolin-7-yloxy)pentanamide, ESI 447;
N-[2-methyl4-(2-oxo-2H-pyridin-1-yl)phenyl]-2-(1-aminoisoquinolin-7-yloxy)-4-methylpentanamide, ESI 457;
N-[3-chloro4-(2-oxo-2H-pyridin-1-yl)phenyl]-2-(1-aminoisoquinolin-7-yloxy)pentanamide, ESI 463;
N-[4-(3-oxomorpholin-4-yl)phenyl]-2-(1-aminoisoquinolin-7-yloxy)-4-methylpentanamide, hydrochloride, ESI 449;
N-[3-trifluoromethyl-4-(3-oxomorpholin4-yl)phenyl]-2-(1-aminoisoquinolin-7-yloxy)-4-methylpentanamide, hydrochloride, ESI 517;
N-[3-trifluoromethyl-4-(3-oxomorpholin4-yl)phenyl]-2-(1-aminoisoquinolin-7-yloxy)pentanamide, hydrochloride, ESI 503.

EXAMPLE 5

N-[4-(2-Oxo-2H-pyridin-1-yl)phenyl]-2-(1-aminoisoquinolin-7-ylamino)-4-methylpentanamide, hydrochloride, ESI 442

The preparation is carried out analogously to the following reaction scheme:

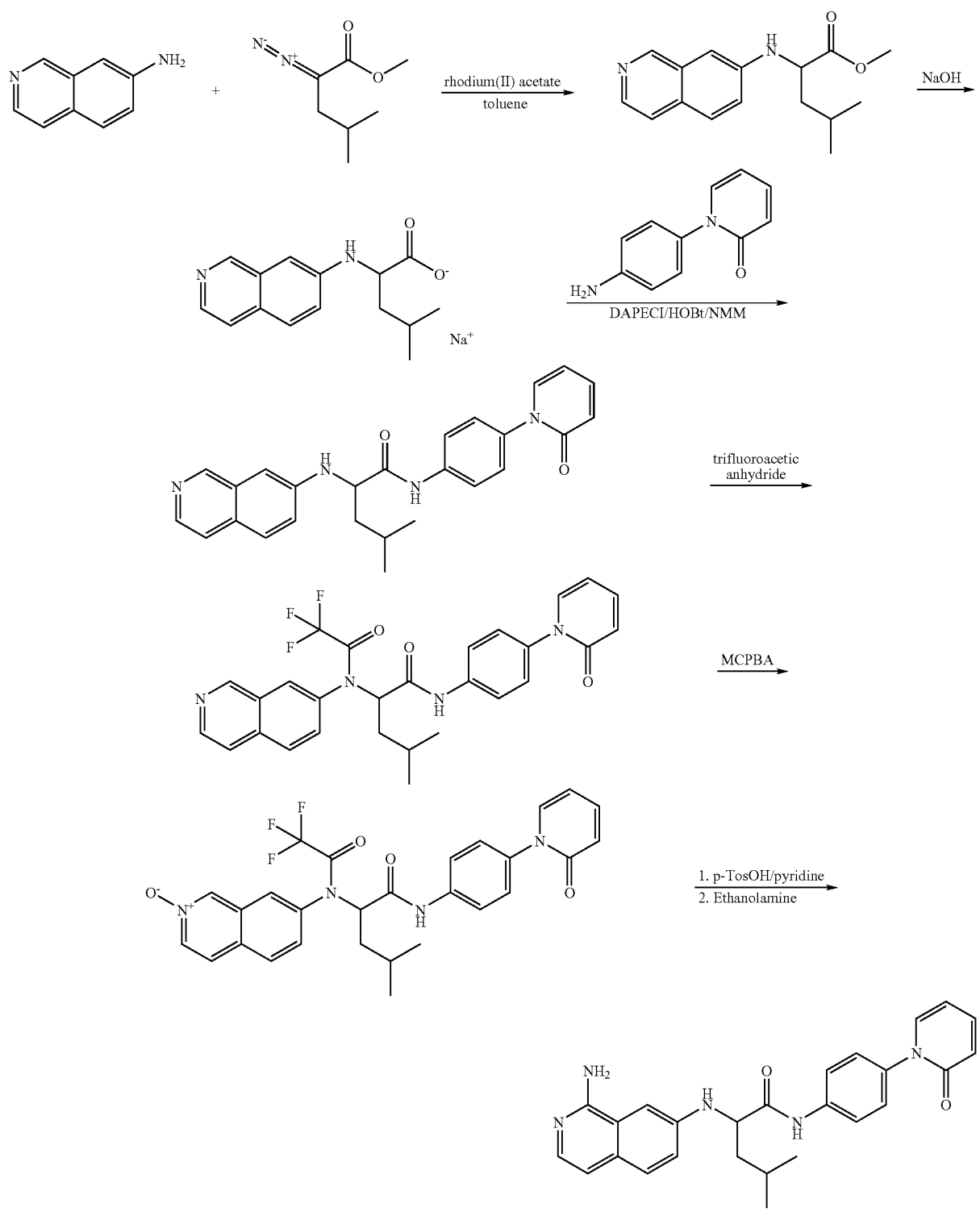

Step 1:

800 mg of rhodium(II) acetate (dimer) are added to a solution of 5.19 g (36.0 mmol) of 7-aminoisoquinoline and 5.47 g (35.0 mmol) of methyl 2-diazo-4-methylpentanoate in 200 ml of toluene, and the mixture is heated at 80° C. for 12 hours. The cooled reaction mixture is filtered, and the filtrate is evaporated. The residue is chromatographed on a silica-gel column with ethyl acetate as eluent, giving methyl 2-(isoquinolin-7-ylamino)-4-methylpentanoate as a yellowish solid; ESI 273.

Step 2:

1 ml of trifluoroacetic anhydride is added to a solution of 200 mg (469 mmol) of N-[4-(2-oxo-2H-pyridin-1-yl)phenyl]-2-[isoquinolin-7-yl-amino)-4-methylpentanamide in 5 ml of dichloromethane, and the mixture is stirred at room temperature for 18 hours. The reaction mixture is partitioned between water and dichloromethane. The organic phase is evaporated, giving N-[4-(2-oxo-2H-pyridin-1-yl)phenyl]-2-[isoquinolin-7-yltrifluoroacetylamino]-4-methylpentanamide as a colourless solid; ESI 523.

The other steps are carried out analogously to Example 1 or by general known procedures.

The following compound is obtained analogously:

N-[4-(3-oxomorpholin-4-yl)phenyl]-(S)-2-(1-aminoisoquinolin-7-ylamino)-4-methylpentanamide, hydrochloride, ESI 448.

EXAMPLE 6

N-[3-Methyl-4-(2-oxopiperidin-1-yl)phenyl]-2-(8-oxo -5,6,7,8-tetrahydronaphthalen-2-yloxy)-2-phenylacetamide and N-[3-methyl-4-(2-oxopiperidin-1-yl)phenyl]-2-(8-amino-5,6,7,8-tetrahydronaphthalen-2-yloxy)-2-phenylacetamide, hydrochloride, ESI 484

The preparation is carried out analogously to the following reaction scheme:

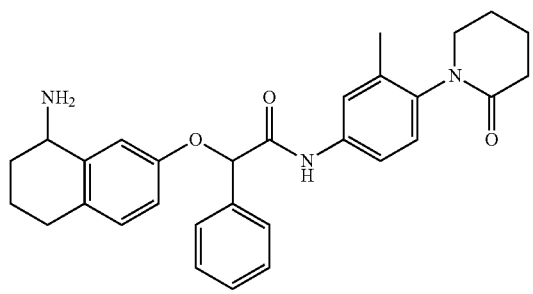

The following is obtained analogously:

N-[3-methyl-4-(2-oxopiperidin-1-yl)phenyl]-2-(8-oxo -5,6,7,8-tetrahydronaphthalen-2-yloxy)-2-(2-fluorophenyl)acetamide, ESI 501.

EXAMPLE 7

N-[4-(2-Oxo-2H-pyridin-1-yl)phenyl]-2-(quinolin-6-ylamino)-2-phenylacetamide, ESI 447

The preparation is carried out analogously to the following reaction scheme:

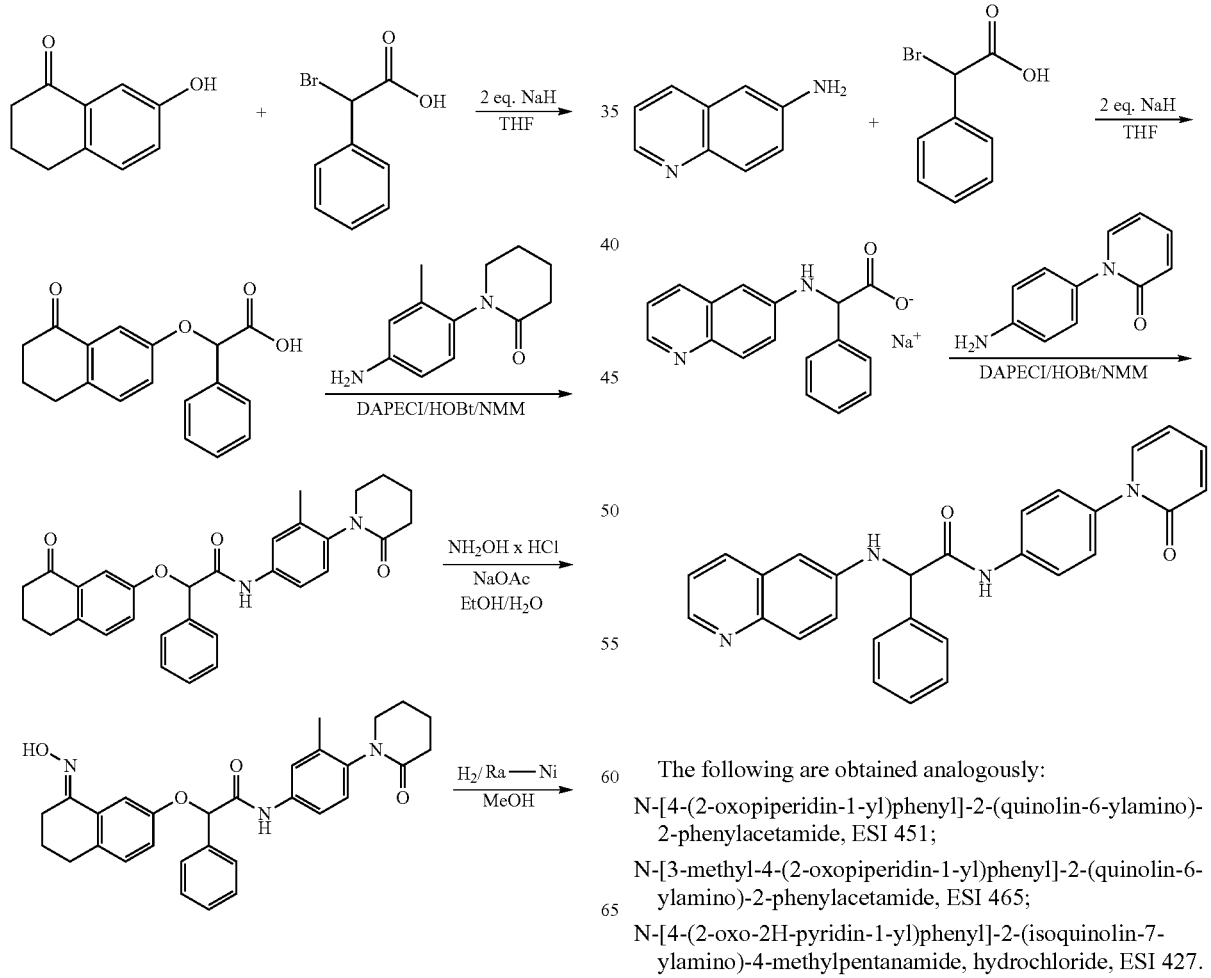

The following are obtained analogously:

N-[4-(2-oxopiperidin-1-yl)phenyl]-2-(quinolin-6-ylamino)-2-phenylacetamide, ESI 451;

N-[3-methyl-4-(2-oxopiperidin-1-yl)phenyl]-2-(quinolin-6-ylamino)-2-phenylacetamide, ESI 465;

N-[4-(2-oxo-2H-pyridin-1-yl)phenyl]-2-(isoquinolin-7-ylamino)-4-methylpentanamide, hydrochloride, ESI 427.

EXAMPLE 8

N-[4-(3-Oxomorpholin-4-yl)phenyl]-2-(3-amino-1H-indazol-5-yloxy)-4-methylpentanamide The preparation is carried out analogously to the following reaction scheme:

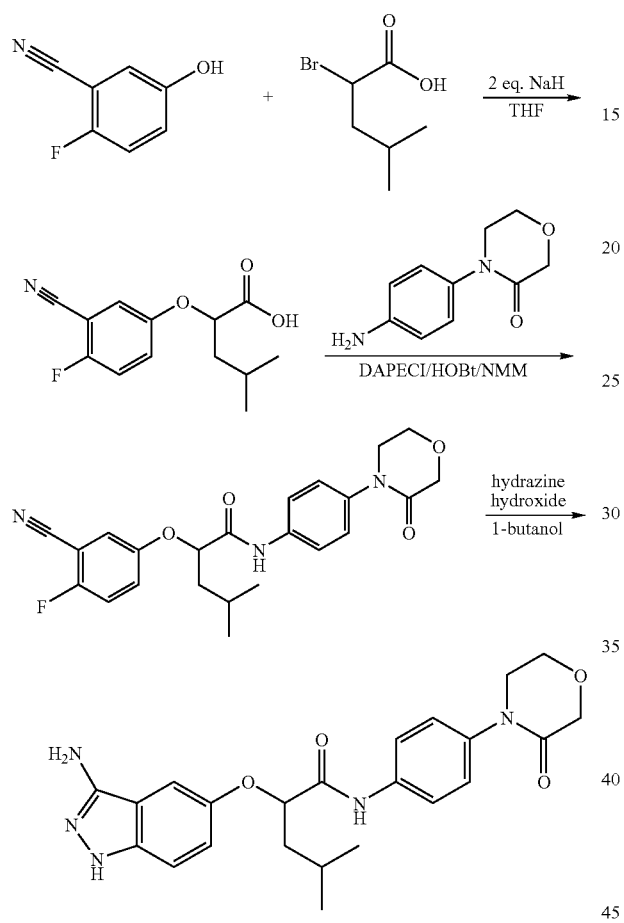

EXAMPLE 9

N-[4-(3-Oxomorpholin-4-yl)phenyl]-2-(3-aminobenzo[d]isoxazol-5-yl-oxy)-4-methylpentanamide The preparation is carried out analogously to the following reaction scheme:

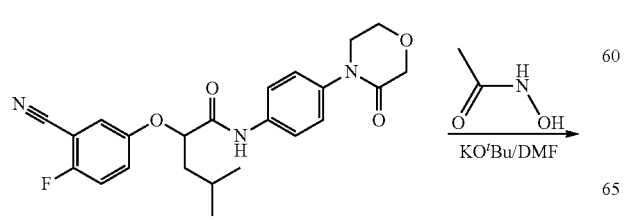

-continued

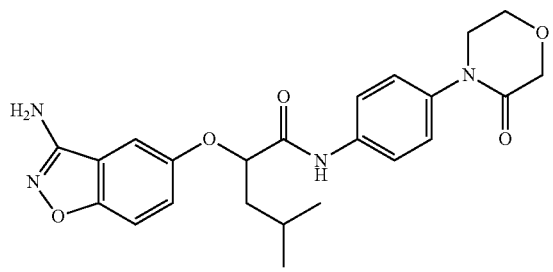

EXAMPLE 10

N-[4-(3-Oxomorpholin4-yl)phenyl]-2-(3-aminobenzo[d]isothiazol-5-ylamino)-2-(2-fluorophenyl)acetamide The preparation is carried out analogously to the following reaction scheme:

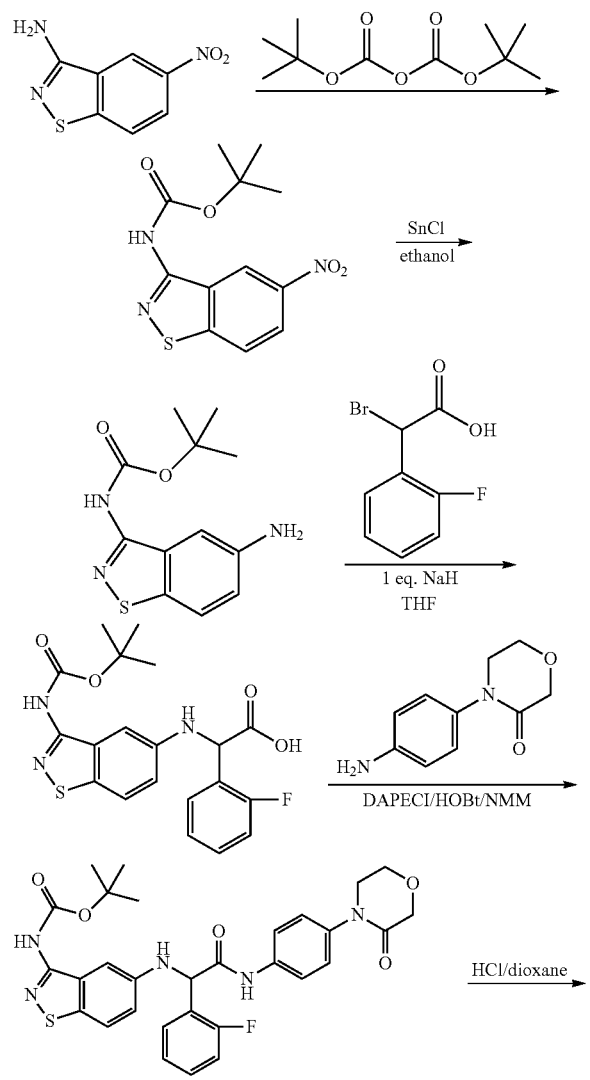

29

-continued

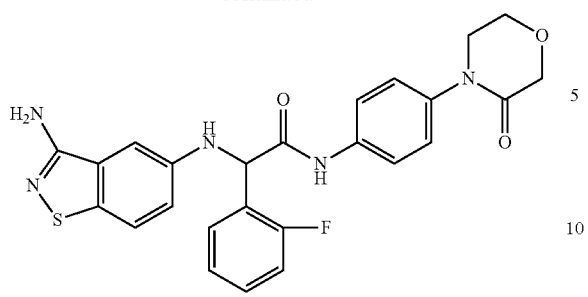

EXAMPLE 11

2-(3-Aminobenzo[c]isothiazol-5-yloxy)-N-[4-(3-oxomorpholin4-yl)-phenyl]-4-methylpentanamide The preparation is carried out analogously to the following reaction scheme:

30

-continued

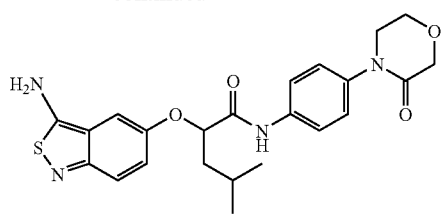

The following is obtained analogously:
N-[4-(3-oxomorpholin-4-yl)phenyl]-2-(3-aminobenzo[d]isothiazol-5-yloxy)-4-methylpentanamide.

EXAMPLE 12

N-[4-(3-Oxomorpholin-4-yl)phenyl]-2-(3-amino-1H-indazol-5-yl-amino)-4-methylpentanamide The preparation is carried out analogously to the following reaction scheme:

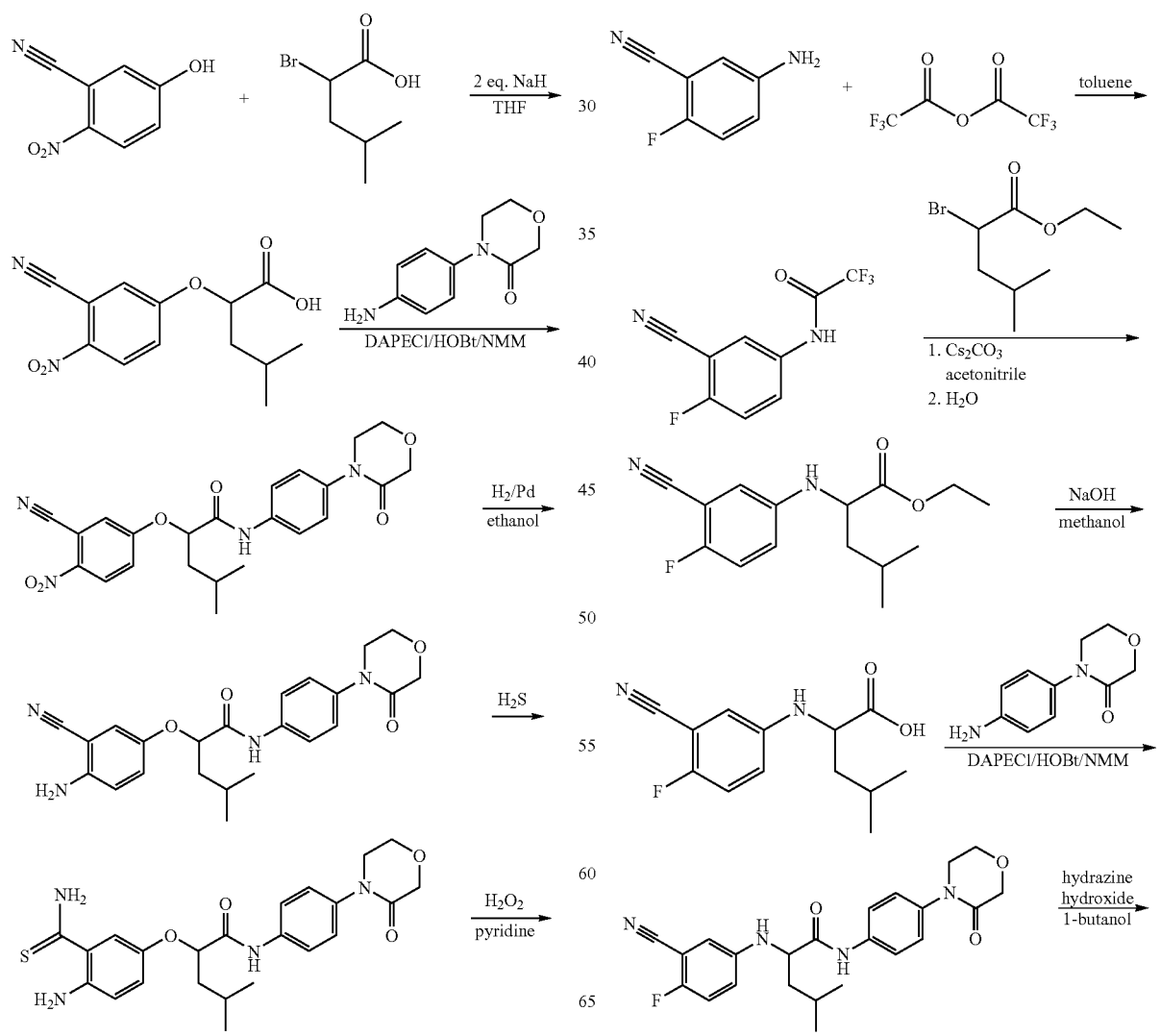

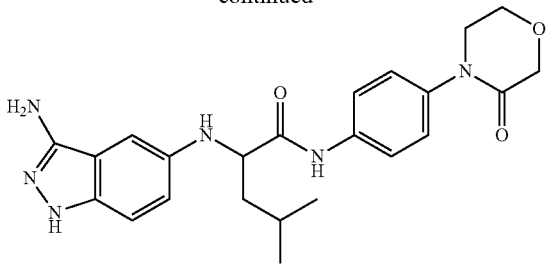

EXAMPLE 13

N-[4-(3-Oxomorpholin-4-yl)phenyl]-2-(3-aminobenzo[d]isoxazol-5-yl-amino)-4-methylpentanamide The preparation is carried out analogously to the following reaction scheme:

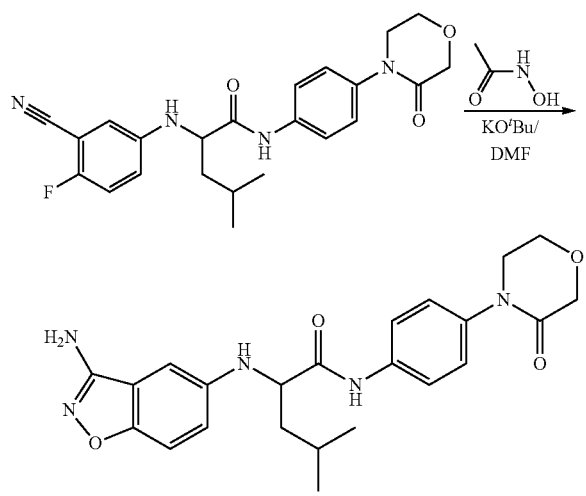

The examples below relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced in a conventional manner into hard gelatine capsules in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

We claim:

1. A compound of the formula I

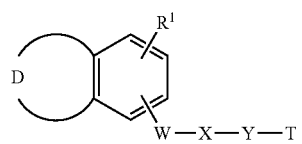

wherein
D is —N=CH—CH=CH—, —CH=N—CH=CH—,
—NH—CO—CH=CH—, —NH—CH=CH—CO—,

—NH—CO—CH$_2$—CH$_2$, or —NH—CH$_2$—CH$_2$—CO—, and wherein, the alkylene chain and/or a nitrogen located therein is optionally mono-, di- or trisubstituted by A or NH$_2$, R$^1$ is H, R$^2$ is H, A, —[C(R$^3$)$_2$]$_n$—Ar, —[C(R$^3$)$_2$]$_n$-Het or —[C(R$^3$)$_2$]$_n$-cycloalkyl, R$^3$ is H or A, W is —C(R$^2$)$_2$—, —[C(R$^2$)$_2$]$_2$—, —OC(R$^2$)$_2$— or —NR$^2$C(R$^2$)$_2$—, X is CONR$^2$, CONR$^2$C(R$^3$)$_2$, —C(R$^3$)$_2$NR$^2$ or —C(R$^3$)$_2$NR$^2$C(R$^3$)$_2$, Y is alkylene, Het-diyl or Ar-diyl, T is a monocyclic or bicyclic, saturated or unsaturated heterocyclic ring having from 1 to 2 N and/or O atoms, which is optionally monosubstituted or disubstituted by carbonyl oxygen, OH or OA, A is unbranched or branched alkyl having 1-6 carbon atoms, in which one or two CH$_2$ groups may be replaced by O or S atoms and/or by —CH=CH— groups and/or in addition 1-7 H atoms may be replaced by F, Ar is phenyl, naphthyl or biphenyl, each of which is unsubstituted or monosubstituted, disubstituted or trisubstituted by Hal, A, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$N(R$^3$)$_2$ or S(O)$_m$A, Het is a monocyclic or bicyclic, saturated, unsaturated or aromatic heterocyclic ring having from 1 to 4 N, O and/or S atoms, which may be unsubstituted or monosubstituted, disubstituted or trisubstituted by carbonyl oxygen, Hal, A, —[C(R$^3$)$_2$]$_n$—Ar, —[C(R$^3$)$_2$]$_n$-Het$^1$, —[C(R$^3$)$_2$]$_n$—cycloalkyl, OR$^2$, N(R$^2$)$_2$, NO$_2$, CN, COOR$^2$, CON(R$^2$)$_2$, NR$^2$COA, NR$^2$CON(R$^2$)$_2$, NR$^2$SO$_2$A, COR$^2$, SO$_2$NR$^2$ and/or S(O)$_m$A, Het$^1$ is a monocyclic or bicyclic, saturated, unsaturated or aromatic heterocyclic ring having 1 or 2 N, O and/or S atoms, which may be unsubstituted or monosubstituted or disubstituted by carbonyl oxygen, Hal, A, OR$^2$, N(R$^2$)$_2$, NO$_2$, CN, COOR$^2$, CON(R$^2$)$_2$, NR$^2$COA, NR$^2$CON(R$^2$)$_2$, NR$^2$SO$_2$A, COR$^2$, SO$_2$NR$^2$ and/or S(O)$_m$A, Hal is F, Cl, Br or I, n is 0, 1 or 2, m is 0, 1 or 2, or a pharmaceutically usable derivative, solvate and stereoisomer thereof, or a mixture thereof.

2. The compound according to claim 1, wherein
W is —C(R$^{2'}$)$_2$—, —[C(R$^{2'}$)$_2$]$_2$—, —OC(R$^{2'}$)$_2$— or —NR$^{2'}$C(R$^{2'}$)$_2$—,
R$^{2'}$ is H, A' or phenyl,
A' is alkyl having 1, 2, 3, 4, 5 or 6 carbon atoms
or a pharmaceutically usable derivative, solvate and stereoisomer thereof, or a mixture thereof.

3. The compound according to claim 1, wherein
X is CONH,
or a pharmaceutically usable derivative, solvate and stereoisomer thereof, or a mixture thereof.

4. The compound according to claim 1, wherein
Y is methylene, ethylene, propylene, or 1,4-phenylene or pyridinediyl, each of which is unsubstituted or monosubstituted by A, Cl, or F,
or a pharmaceutically usable derivative, solvate or stereoisomer thereof, or a mixture thereof.

5. The compound according to claim 1, wherein
Y is 1,3- or 1,4-phenylene which is unsubstituted or monosubstituted by methyl, ethyl, propyl, Cl, F or trifluoromethyl,
or a pharmaceutically usable derivative, solvate and stereoisomer thereof, or a mixture thereof.

6. The compound according to claim 1, wherein
T is 2-oxopiperidin-1-yl, 2-oxopyrrolidin-1-yl, 2-oxo-1H pyridin-1-yl, 3-oxomorpholin-4-yl, 4-oxo-1H-pyridin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-oxoazepan-1-yl, 2-hydroxy-6-oxopiperazin-1-yl, 2-azabicyclo[2.2.2]octan-3-on-2-yl or 2-methoxy-6-oxopiperazin-1-yl,
or a pharmaceutically usable derivative, solvate or stereoisomer thereof, or a mixture thereof.

7. The compound according to claim 1, wherein
D is N=CH—CH=CH, CH=N—CH=CH, NH—CO—CH=CH, NH—CH=CH—CO, NH—CO—CH$_2$—CH$_2$, or NH—CH$_2$—CH$_2$—CO,
and wherein, the alkylene chain and/or a nitrogen located therein is optionally mono-, di- or trisubstituted by A or NH$_2$,
R$^1$ is H,
W is —C(R$^{2'}$)$_2$—, —[C(R$^{2'}$)$_2$]$_2$—, —OC(R$^{2'}$)$_2$— or —NR$^{2'}$C(R$^{2'}$)$_2$—,
R$^{2'}$ is H, A' or phenyl,
A' is alkyl having 1, 2, 3, 4, 5 or 6 carbon atoms,
X is CONH,
Y is 1,3- or 1,4-phenylene which is unsubstituted or monosubstituted by methyl, ethyl, propyl, Cl, F or trifluoromethyl,
T is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-oxoazepan-1-yl, 2-hydroxy-6-oxopiperazin-1-yl, 2-azabicyclo[2.2.2]octan-3-on-2-yl or 2-methoxy-6-oxopiperazin-1-yl,
or a pharmaceutically usable derivative, solvate and stereoisomer thereof, or a mixture thereof.

8. The compound according to claim 1, which is
N-[4-(2-oxopiperidin-1-yl)phenyl]-2-(isoquinolin-7-yloxy)-2-phenylacetamide,
N-[4-(2-oxopiperidin-1-yl)phenyl]-2-(1-aminoisoquinolin-7-yloxy)-2-phenylacetamide,
N-[4-(2-oxopiperidin-1-yl)phenyl]-2-(isoquinolin-7-yloxy)-2-phenyl-acetamide,
N-[4-(2-oxopiperidin-1-yl)phenyl]-2-(isoquinolin-7-yloxy)pentanamide,
N-[4-(2-oxopiperidin-1-yl)phenyl]-2-(1-aminoisoquinolin-7-yl-oxy)acetamide,
N-[4-(2-oxopiperidin-1-yl)phenyl]-2-(isoquinolin-7-yloxy)acetamide,
N-[4-(2-oxopyrrolidin-1-yl)-3-methylphenyl]-2-(isoquinolin-7-yl-oxy)pentanamide,
N-[4-(2-oxopiperidin-1-yl)-3-methylphenyl]-2-(isoquinolin-7-yl-oxy)pentanamide,
N-[4-(2-oxoazepan-1-yl)-3-methylphenyl]-2-(isoquinolin-7-yl-oxy)pentanamide,
N-[4-(2-oxopiperidin-1-yl)-3-methylphenyl]-2-(isoquinolin-7-yl-oxy)acetamide,
N-[4-(2-oxopiperidin-1-yl)-3-methylphenyl]-2-(isoquinolin-7-ylamino)-2-phenylacetamide,
N-[4-(2-oxopiperidin-1-yl)-3-methylphenyl]-2-(isoquinolin-6-ylamino)-2-phenylacetamide,
N-[4-(2-oxopiperidin-1-yl)-3-methylphenyl]-2-(quinoxalin-6-ylamino)-2-phenylacetamide, N-[3-methyl-4-(2-oxopiperidin-1-yl)phenyl]-2-(isoquinolin -7-yloxy)-2-(2-fluorophenyl)acetamide,
N-[4-(2-oxo-1H-pyrazin-1-yl)phenyl]-2-(isoquinolin-7-yloxy)-pentanamide,
N-[4-(3-oxomorpholin-4-yl)phenyl]-(S)-2-(1-aminoisoquinolin-7-yl-oxy)-4-methylpentanamide,
N-[3-methyl-4-(3-oxomorpholin-4-yl)phenyl]-(S)-2-(1-aminoisoquinolin-7-yloxy)-4-methylpentanamide,
N-[4-(2-oxo-2H-pyridin-1-yl)phenyl]-(S)-2-(1-aminoisoquinolin-7-yl-oxy)-4-methylpentanamide,
N-[4-(3-oxomorpholin-4-yl)phenyl]-2-(1-aminoisoquinolin-7-yl-oxy)pentanamide,
N-[4-(3-oxomorpholin-4-yl)phenyl]-2-(1-aminoisoquinolin-7-yloxy)-2-(2-chlorophenyl)acetamide,
N-[4-(3-oxo-2H-pyridazin-2-yl)phenyl]-2-(1-aminoisoquinolin-7-yl-oxy)-4-methylpentanamide,
N-[4-(2-oxo-1H-pyrazin-1-yl)phenyl]-2-(1-aminoisoquinolin-7-yl-oxy)-4-methylpentanamide,
N-[4-(2-oxopiperazin-1-yl)phenyl]-2-(1-aminoisoquinolin-7-yloxy)-4-methylpentanamide,
N-[4-(2-oxo-1,3-oxazinan-3-yl)phenyl]-2-(1-aminoisoquinolin-7-yl-oxy)-4-methylpentanamide,
N-[4-(2-oxo-3H-thiazol-3-yl)phenyl]-2-(1-aminoisoquinolin-7-yloxy)-4-methylpentanamide,
N-[4-(2-oxooxazolidin-3-yl)phenyl]-2-(1-aminoisoquinolin-7-yloxy)-4-methylpentanamide,
N-[3-methyl-4-(2-oxooxazolidin-3-yl)phenyl]-2-(1-aminoisoquinolin-7-yloxy)-4-methylpentanamide,
N-[4-(2-oxotetrahydropyrimidin-1-yl)phenyl]-2-(1-aminoisoquinolin-7-yloxy)-4-methylpentanamide,
N-[4-(2-oxoimidazolidin-1-yl)phenyl]-2-(1-aminoisoquinolin -7-yl-oxy)-4-methylpentanamide,
N-[3-methyl-4-(2-oxoazepan-1-yl)phenyl]-2-(1-aminoisoquinolin-7-yloxy)pentanamide,
N-[3-methyl-4-(2-oxopiperidin-1-yl)phenyl]-2-(1-aminoisoquinolin-7-yloxy)pentanamide,
N-[3-methyl-4-(2-oxopiperidin-1-yl)phenyl]-2-(1-aminoisoquinolin-7-yloxy)acetamide,
N-[3-trifluoromethyl-4-(2-azabicyclo[2.2.2]octan-3-on-2-yl)phenyl]-2-(1-aminoisoquinolin-7-yloxy)pentanamide,
N-[4-(2-oxopiperidin-1-yl)phenyl]-2-(1-aminoisoquinolin-7-yl-oxy)propionamide,
N-[4-(2-oxopiperidin-1-yl)phenyl]-2-(1-aminoisoquinolin-7-yl-oxy)butyramide,
N-[3-methyl-4-(2-oxopyrrolidin-1-yl)phenyl]-2-(1-aminoisoquinolin-7-yloxy)butyramide,
N-[4-(2-oxopiperidin-1-yl)phenyl]-2-(1-aminoisoquinolin-7-yl-oxy)pentanamide,
N-[4-(2-oxopyrrolidin-1-yl)phenyl]-2-(1-aminoisoquinolin-7-yl-oxy)hexanamide,
N-[3-methyl-4-(2-oxopiperidin-1-yl)phenyl]-2-(1-aminoisoquinolin-7-yloxy)hexanamide,
N-[4-(2-oxo-2H-pyridin-1-yl)phenyl]-2-(1-aminoisoquinolin-7-yl-oxy)butyramide,
N-[4-(2-oxo-2H-pyridin-1-yl)phenyl]-2-(1-aminoisoquinolin-7-yl-oxy)pentanamide,
N-[3-chloro-4-(2-oxopyrrolidin-1-yl)phenyl]-2-(1-aminoisoquinolin-7-yl-oxy)pentanamide,
N-[3-methyl-4-(2-oxopiperidin-1-yl)phenyl]-2-(1-aminoisoquinolin-7-yloxy)butyramide,
N-[4-(2-oxopiperidin-1-yl)phenyl]-2-(1-aminoisoquinolin-7-yl-oxy)hexanamide,
N-[4-(2-oxopiperidin-1-yl)phenyl]-2-(1-aminoisoquinolin-7-yloxy)-4-methylpentanamide,
N-[3-methyl-4-(2-oxopiperidin-1-yl)phenyl]-2-(1-aminoisoquinolin-7-yloxy)-4-methylpentanamide, hydrochloride, ESI 461;
N-[4-(2-oxo-2H-pyridin-1-yl)phenyl]-2-(1-aminoisoquinolin-7-yl-oxy)-4-methylpentanamide,
N-[4-(2-oxopiperidin-1-yl)phenyl]-2-(1-aminoisoquinolin-7-yloxy)-2-(2-fluorophenyl)acetamide,
N-[3-methyl-4-(2-oxopiperidin-1-yl)phenyl]-2-(1-aminoisoquinolin-7-yloxy)-2-(2-fluorophenyl)acetamide,
N-[4-(2-oxo-2H-pyridin-1-yl)phenyl]-(R)-2-(1-aminoisoquinolin-7-yl-oxy)-4-methylpentanamide,
N-[4-(2-oxo-2H-pyridin-1-yl)phenyl]-2-(1-aminoisoquinolin-7-yl-oxy)-4,4-dimethylpentanamide,
N-[4-(2-oxo-2H-pyridin-1-yl)phenyl]-2-(1-aminoisoquinolin-7-yl-oxy)-2-(2-fluorophenyl)acetamide,
N-[4-(3-oxomorpholin-4-yl)phenyl]-2-(1-aminoisoquinolin-7-yl-oxy)butyramide,
N-[3-methyl-4-(3-oxomorpholin-4-yl)phenyl]-2-(1-aminoisoquinolin-7-yloxy)butyramide,
N-[3-methyl-4-(3-oxomorpholin-4-yl)phenyl]-2-(1-aminoisoquinolin-7-yloxy)pentanamide,
N-[3-chloro-4-(2-oxo-2H-pyridin-1-yl)phenyl]-2-(1-aminoisoquinolin-7-yloxy)-4-methylpentanamide,
N-[4-(3-oxomorpholin-4-yl)phenyl]-2-(1-aminoisoquinolin-7-yloxy)-2-(2-fluorophenyl)acetamide,
N-[3-methyl-4-(3-oxomorpholin-4-yl)phenyl]-2-(1-aminoisoquinolin-7-yloxy)-4-methylpentanamide,
N-[3-chloro-4-(2-oxopyrrolidin-1-yl)phenyl]-2-(1-aminoisoquinolin-7-yloxy)-2-(2-fluorophenyl)acetamide,
N-[3-chloro-4-(2-oxo-2H-pyridin-1-yl)phenyl]-2-(1-aminoisoquinolin-7-yloxy)butyramide,
N-[2-fluoro-4-(2-oxo-2H-pyridin-1-yl)phenyl]-2-(1-aminoisoquinolin-7-yloxy)pentanamide,
N-[2-methyl-4-(2-oxo-2H-pyridin-1-yl)phenyl]-2-(1-aminoisoquinolin-7-yloxy)-4-methylpentanamide,
N-[3-chloro-4-(2-oxo-2H-pyridin-1-yl)phenyl]-2-(1-aminoisoquinolin-7-yloxy)pentanamide,
N-[4-(3-oxomorpholin-4-yl)phenyl]-2-(1-aminoisoquinolin-7-yloxy)-4-methylpentanamide,
N-[3-trifluoromethyl-4-(3-oxomorpholin-4-yl)phenyl]-2-(1-aminoisoquinolin-7-yloxy)-4-methylpentanamide,
N-[3-trifluoromethyl-4-(3-oxomorpholin-4-yl)phenyl]-2-(1-aminoisoquinolin-7-yloxy)pentanamide,
N-[4-(2-oxo-2H-pyridin-1-yl)phenyl]-2-(1-aminoisoquinolin-7-ylamino)-4-methylpentanamide,
N-[4-(3-oxomorpholin-4-yl)phenyl]-(S)-2-(1-aminoisoquinolin-7-ylamino)-4-methylpentanamide,
N-[4-(2-oxo-2H-pyridin-1-yl)phenyl]-2-(quinolin-6-ylamino)-2-phenylacetamide,
N-[4-(2-oxopiperidin-1-yl)phenyl]-2-(quinolin-6-ylamino)-2-phenylacetamide,
N-[3-methyl-4-(2-oxopiperidin-1-yl)phenyl]-2-(quinolin-6-ylamino)-2-phenylacetamide, or
N-[4-(2-oxo-2H-pyridin-1-yl)phenyl]-2-(isoquinolin-7-ylamino)-4-methylpentanamide, or a pharmaceutically usable derivatives, solvates and stereoisomers thereof, or a mixture thereof.

9. A process for the preparation of a compound according to claim 1 comprising a) for the preparation of a compound of the formula I in which W is —OC(R$^2$)$_2$— or —NR$^2$C(R$^2$)$_2$—, reacting a compound of the formula II

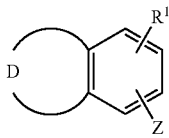

wherein
Z is OH or NHR², and
R¹, R² and D are as defined in claim 1, with the proviso that any further OH and/or amino group present is protected,
with a compound of the formula III

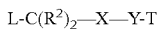

L-C(R²)₂—X—Y-T  III wherein
L is Cl, Br or I, and R², X, Y and T are as defined in claim 1, and
cleaving and protecting group,
or
b) for the preparation of a compound of the formula I in which X is CONR² or CONR²C(R³)₂,
reacting a compound of the formula IV

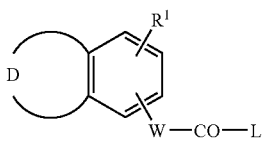

wherein
L is Cl, Br, I or a free or reactively functionally modified OH group,
and
R¹, W and D are as defined in claim 1, with the proviso that any further OH and/or amino group present is protected,
with a compound of the formula V

Z'—Y-T  V wherein
Z' is NHR²or NHR²C(R³)₂, and
R², Y and T are as defined in claim 1, and
cleaving and protecting group,
and/or converting a base or an acid of formula I into a salt.

10. A method of inhibiting the activity of coagulation factor Xa comprising contacting said coagulation factor Xa with a compound of claim 1.

11. A method of inhibiting the activity of coagulation factor VIIa comprising contacting said coagulation factor VIIa with a compound of claim 1.

12. A medicament comprising at least one compound of claim 1 and optionally comprising an excipient and/or assistant.

13. A medicament comprising at least one compound of claim 1 and at least one further medicament active ingredient.

14. A method for treating thromboses, myocardial infarction, arteriosclerosis, inflammation, apoplexia, angina pectoris, restenosis after angioplasty, claudicatio intermittens, migraine, tumours, tumour diseases and/or tumour metastases comprising administering to a host in need thereof an effective amount of a compound of claim 1.

15. A method for treating thromboses, myocardial infarction, arteriosclerosis, inflammation, apoplexia, angina pectoris, restenosis after angioplasty, claudicatio intermittens, migraine, tumours, tumour diseases and/or tumour metastases comprising administering to a host in need thereof an effective amount of a medicament of claim 13.

16. A compound according to claim 1, wherein D is N=CH—CH=CH, CH=N—CH=CH, NH—CO—CH=CH, NH—CH=CH—CO, NH—CO—CH₂—CH₂, or NH—CH₂—CH₂—CO, and wherein, the alkylene chain and/or a nitrogen located therein is optionally monosubstituted by A or NH₂.

17. A compound according to claim 1, wherein W is —OC(R²)₂— or —NR²C(R²)₂—, X is CONR², Y is Ar-diyl, and T is 2-oxopiperidin—1-yl, 2-oxopyrrolidin-1-yl, 2-oxoazepan-1-yl, 2-oxo-2H-pyrazin-1-yl, 3-oxomorpholin-4-yl, 2-oxo-2H-pyridin-1-yl, 3-oxo-2H-pyridazin-1-yl, 2-oxopiperazin-1-yl, 2-oxo-1,3-oxazinan-3-yl, 2-oxo-3H-thiazol-3-yl, 2-oxooxazolidin-3-yl, 2-oxotetrahydropyrimidin-1-yl, 2-oxoimidazolidin-1-yl, or 2-azabicyclo[2.2.2]octan-3-on-2yl.

18. A compound according to claim 17, wherein Y is phenylene.

19. A compound according to claim 17, wherein R² is H, alkyl having 1-6 carbon atoms or phenyl.

20. A compound according to claim 18, wherein R² is H, alkyl having 1-6 carbon atoms or phenyl.

21. A compound according to claim 16, wherein W is —OC(R²)₂— or —NR²C(R²)₂—, X is CONR², Y is Ar-diyl, and T is 2-oxopiperidin-1-yl, 2-oxopyrrolidin-1-yl, 2-oxoazepan-1-yl, 2-oxo-2H-pyrazin-1-yl, 3-oxomorpholin-4-yl, 2-oxo-2H-pyridin-1-yl, 3-oxo-2H-pyridazin-1-yl, 2-oxopiperazin-1-yl, 2-oxo-1,3-oxazinan-3-yl, 2-oxo-3H-thiazol-3-yl, 2-oxooxazolidin-3-yl, 2-oxotetrahydropyrimidin-1-yl, 2-oxoimidazolidin-1-yl, or 2-azabicyclo[2.2.2]octan-3-on-2yl.

22. A compound according to claim 21, wherein Y is phenylene.

23. A compound according to claim 21, wherein R² is H, alkyl having 1-6 carbon atoms or phenyl.

24. A compound according to claim 22, wherein R² is H, alkyl having 1-6 carbon atoms or phenyl.

25. A method for treating thromboses, myocardial infarction, arteriosclerosis, inflammation, apoplexia, angina pectoris, restenosis after angioplasty, or claudicatio intermittens comprising administering to a host in need thereof an effective amount of a compound of claim 1.

26. A method for treating thromboses, myocardial infarction, arteriosclerosis, inflammation, apoplexia, angina pectoris, restenosis after angioplasty, or claudicatio intermittens comprising administering to a host in need thereof an effective amount of a pharmaceutical composition of claim 13.

* * * * *

UNITED STATES PATENT AND TRADEMARK OFFICE
CERTIFICATE OF CORRECTION

| | |
|---|---|
| PATENT NO. | : 7,902,223 B2 |
| APPLICATION NO. | : 10/486238 |
| DATED | : March 8, 2011 |
| INVENTOR(S) | : Dorsch et al. |

Page 1 of 1

It is certified that error appears in the above-identified patent and that said Letters Patent is hereby corrected as shown below:

Column 33, line 52 reads "or a pharmaceutically usable derivative, solvate and stereoi-"
Should read --or a pharmaceutically usable derivative, solvate or stereoi--.

Column 33, line 56 reads "or a pharmaceutically usable derivative, solvate and stereoi-"
Should read --or a pharmaceutically usable derivative, solvate or stereoi- --.

Column 34, line 1 reads "or a pharmaceutically usable derivative, solvate and stereoi-"
Should read --or a pharmaceutically usable derivative, solvate or stereoi--.

Column 34, line 39 reads "or a pharmaceutically usable derivative, solvate and stereoi-"
Should read --or a pharmaceutically usable derivative, solvate or stereoi--.

Column 36, line 61 reads "or a pharmaceutically usable derivatives, solvates and stere-"
Should read --or a pharmaceutically usable derivative, solvate or stere- --.

Column 36, line 62 reads "oisomers thereof, or a mixture thereof"
Should read --oisomer thereof, or a mixture thereof.--.

Column 37, line 22 reads "cleaving and protecting group,"
Should read --cleaving said protecting group,--.

Column 37, line 50 reads "cleaving and protecting group"
Should read --cleaving said protecting group--.

Column 37, line 60 reads "claim 1 and optionally comprising an excipient and/or assis-"
Should read --claim 1 and optionally comprising an excipient and/or an assis- --.

Signed and Sealed this
Thirteenth Day of March, 2012

David J. Kappos
*Director of the United States Patent and Trademark Office*